United States Patent
Leigh et al.

(10) Patent No.: US 10,576,276 B2
(45) Date of Patent: Mar. 3, 2020

(54) IMPLANTED MAGNET MANAGEMENT IN THE FACE OF EXTERNAL MAGNETIC FIELDS

(71) Applicant: Cochlear Limited, Macquarie University (AU)

(72) Inventors: Charles Roger Aaron Leigh, Macquarie University (AU); Anthony Powell, Macquarie University (AU); Peter Raymond Sibary, Macquarie University (AU)

(73) Assignee: Cochlear Limited, Macquarie University, NSW (AU)

( * ) Notice: Subject to any disclaimer, the term of this patent is extended or adjusted under 35 U.S.C. 154(b) by 268 days.

(21) Appl. No.: 15/581,937

(22) Filed: Apr. 28, 2017

(65) Prior Publication Data
US 2017/0312503 A1 Nov. 2, 2017

Related U.S. Application Data

(60) Provisional application No. 62/329,240, filed on Apr. 29, 2016.

(51) Int. Cl.
*A61N 1/08* (2006.01)
*A61N 1/36* (2006.01)
*G01R 33/28* (2006.01)

(52) U.S. Cl.
CPC ............ *A61N 1/08* (2013.01); *A61N 1/36038* (2017.08); *G01R 33/285* (2013.01); *G01R 33/288* (2013.01)

(58) Field of Classification Search
CPC ...... G01R 33/285; G01R 33/288; A61N 1/08; A61N 1/36038
See application file for complete search history.

(56) References Cited

U.S. PATENT DOCUMENTS

| | | |
|---|---|---|
| 3,043,000 A | 7/1962 | Hatfield |
| 3,487,403 A | 12/1969 | Pihl |
| 3,573,812 A | 4/1971 | Pihl |
| D227,118 S | 6/1973 | Muraoka |
| 3,771,685 A | 11/1973 | Micallef |
| 3,801,767 A | 4/1974 | Marks |
| 3,987,967 A | 10/1976 | Kuznetsov et al. |

(Continued)

FOREIGN PATENT DOCUMENTS

| | | |
|---|---|---|
| GB | 414579 A | 8/1934 |
| GB | 2266045 A | 10/1993 |

OTHER PUBLICATIONS

MED-EL, "FDA Hands MED-EL Approval for MRI Compatible Cochlear Implant (Video)," believed to be available in Jan. 2015.

(Continued)

*Primary Examiner* — Christine H Matthews
*Assistant Examiner* — Joshua Daryl D Lannu
(74) *Attorney, Agent, or Firm* — Pilloff Passino & Cosenza LLP; Martin J. Cosenza

(57) ABSTRACT

A method, including subjecting a subcutaneous medical device containing a magnet to a magnetic field, thereby imparting a torque onto the magnet, and resisting the imparted torque via an external device that has a skin facing component extending in a direction away from a curvature of the body of the recipient at locations proximate a portion directly contacting skin directly above the implanted magnet.

20 Claims, 20 Drawing Sheets

(56) References Cited

U.S. PATENT DOCUMENTS

| | | |
|---|---|---|
| 4,003,521 A | 1/1977 | Hess |
| 4,038,990 A | 8/1977 | Thompson |
| 4,197,840 A | 4/1980 | Beck et al. |
| 4,199,741 A | 4/1980 | Paulet |
| 4,226,164 A | 10/1980 | Carter |
| 4,240,428 A | 12/1980 | Akhavi |
| 4,257,936 A | 3/1981 | Matsumoto et al. |
| 4,317,969 A | 3/1982 | Riegler et al. |
| D267,541 S | 1/1983 | Kanemitsu |
| 4,414,701 A | 11/1983 | Johnson |
| 4,596,971 A | 6/1986 | Hirabayashi et al. |
| 4,606,329 A | 8/1986 | Hough |
| 4,610,621 A | 9/1986 | Taber et al. |
| 4,628,907 A | 12/1986 | Epley |
| 4,676,772 A | 6/1987 | Hooven |
| 4,726,378 A | 2/1988 | Kaplan |
| 4,731,718 A | 3/1988 | Sheu |
| 4,736,747 A | 4/1988 | Drake |
| RE32,947 E | 6/1989 | Dormer et al. |
| 4,868,530 A | 9/1989 | Ahs |
| 4,917,504 A | 4/1990 | Scott et al. |
| 4,918,745 A | 4/1990 | Hutchison |
| 4,920,679 A | 5/1990 | Sarles et al. |
| 5,014,592 A | 5/1991 | Zweig et al. |
| 5,015,224 A | 5/1991 | Maniglia |
| 5,096,763 A | 3/1992 | Ogata et al. |
| 5,105,811 A | 4/1992 | Kuzma |
| 5,183,056 A | 2/1993 | Dalen et al. |
| 5,196,710 A | 3/1993 | Kalfaian |
| 5,314,453 A | 5/1994 | Jeutter |
| D348,067 S | 6/1994 | Lucey et al. |
| 5,456,654 A | 10/1995 | Ball |
| 5,554,096 A | 9/1996 | Ball |
| 5,603,726 A | 2/1997 | Schulman et al. |
| 5,624,376 A | 4/1997 | Ball et al. |
| 5,630,835 A | 5/1997 | Brownlee |
| 5,716,407 A | 2/1998 | Knapp et al. |
| 5,749,912 A | 5/1998 | Zhang et al. |
| 5,775,652 A | 7/1998 | Crawshaw et al. |
| 5,785,477 A | 7/1998 | McGuffey et al. |
| 5,800,336 A | 9/1998 | Ball et al. |
| 5,857,958 A | 1/1999 | Ball et al. |
| 5,877,664 A | 3/1999 | Jackson, Jr. |
| 5,897,486 A | 4/1999 | Ball et al. |
| 5,913,815 A | 6/1999 | Ball et al. |
| 5,971,334 A | 10/1999 | Crawshaw et al. |
| 6,040,762 A | 3/2000 | Tompkins |
| 6,073,973 A | 6/2000 | Boscaljon et al. |
| 6,138,681 A | 10/2000 | Chen et al. |
| 6,157,278 A | 12/2000 | Katznelson et al. |
| 6,157,281 A | 12/2000 | Katznelson et al. |
| 6,175,767 B1 | 1/2001 | Doyle, Sr. |
| 6,178,079 B1 | 1/2001 | Renger |
| 6,178,353 B1 | 1/2001 | Griffith et al. |
| 6,190,305 B1 | 2/2001 | Ball et al. |
| 6,208,235 B1 | 3/2001 | Trontelj |
| 6,208,882 B1 | 3/2001 | Lenarz et al. |
| 6,217,508 B1 | 4/2001 | Ball et al. |
| 6,219,580 B1 | 4/2001 | Faltys et al. |
| 6,244,142 B1 | 6/2001 | Swanson |
| 6,259,951 B1 | 7/2001 | Kuzma et al. |
| 6,263,230 B1 | 7/2001 | Haynor et al. |
| 6,272,382 B1 | 8/2001 | Faltys et al. |
| 6,292,678 B1 | 9/2001 | Hall et al. |
| 6,295,472 B1 | 9/2001 | Rubinstein et al. |
| 6,295,473 B1 | 9/2001 | Rosar |
| 6,308,101 B1 | 10/2001 | Faltys et al. |
| 6,313,551 B1 | 11/2001 | Hazelton |
| 6,348,070 B1 | 2/2002 | Teissl et al. |
| 6,358,281 B1 | 3/2002 | Berrang et al. |
| 6,401,723 B1 | 6/2002 | Garibaldi et al. |
| 6,475,134 B1 | 11/2002 | Ball et al. |
| 6,505,062 B1 | 1/2003 | Ritter et al. |
| 6,506,987 B1 | 1/2003 | Woods |
| 6,522,909 B1 | 2/2003 | Garibaldi et al. |
| 6,542,777 B1 | 4/2003 | Griffith et al. |
| 6,571,676 B1 | 6/2003 | Folsom et al. |
| 6,668,065 B2 | 12/2003 | Lee et al. |
| 6,838,963 B2 | 1/2005 | Zimmerling et al. |
| 6,857,612 B2 | 2/2005 | Goodbred |
| D512,416 S | 12/2005 | Malaver |
| 6,991,594 B2 | 1/2006 | Holcomb |
| 7,091,806 B2 | 8/2006 | Zimmerling et al. |
| 7,190,247 B2 | 3/2007 | Zimmerling |
| 7,200,504 B1 | 4/2007 | Fister |
| 7,225,028 B2 | 5/2007 | Della Santina et al. |
| 7,231,252 B2 | 6/2007 | Duncan et al. |
| 7,338,028 B2 | 3/2008 | Zimmerling et al. |
| 7,566,296 B2 | 7/2009 | Zimmerling et al. |
| 7,610,096 B2 | 10/2009 | McDonald, III |
| 7,642,887 B2 | 1/2010 | Zimmerling |
| 7,647,120 B2 | 1/2010 | Della Santina et al. |
| 7,695,427 B2 | 4/2010 | Kugler et al. |
| 7,856,986 B2 | 12/2010 | Darley |
| 7,976,453 B2 | 7/2011 | Zimmerling et al. |
| 7,991,477 B2 | 8/2011 | McDonald, III |
| 8,013,699 B2 | 9/2011 | Zimmerling |
| 8,118,725 B2 | 2/2012 | Zimmerling et al. |
| 8,211,174 B2 | 7/2012 | Park et al. |
| 8,255,058 B2 | 8/2012 | Gibson et al. |
| 8,260,435 B2 | 9/2012 | Johnson et al. |
| 8,270,647 B2 | 9/2012 | Crawford et al. |
| 8,340,774 B2 | 12/2012 | Hochmair et al. |
| 8,515,112 B2 | 8/2013 | Crawford et al. |
| 8,515,544 B2 | 8/2013 | Daly et al. |
| 8,532,783 B2 | 9/2013 | Zimmerling et al. |
| 8,634,909 B2 | 1/2014 | Zimmerling et al. |
| 8,734,475 B2 | 5/2014 | Ekvall et al. |
| 8,744,106 B2 | 6/2014 | Ball |
| 8,758,394 B2 | 6/2014 | Zimmerling et al. |
| 8,768,480 B2 | 7/2014 | Charvin |
| 8,897,475 B2 | 11/2014 | Ball et al. |
| 8,983,102 B2 | 3/2015 | Crawford et al. |
| 9,022,917 B2 | 5/2015 | Kasic et al. |
| RE45,701 E | 9/2015 | Zimmerling et al. |
| 9,144,676 B2 | 9/2015 | Gibson et al. |
| 2001/0021805 A1 | 9/2001 | Blume et al. |
| 2002/0076071 A1 | 6/2002 | Single |
| 2003/0120202 A1 | 6/2003 | Gordon |
| 2003/0139782 A1 | 7/2003 | Duncan |
| 2003/0171787 A1 | 9/2003 | Money et al. |
| 2003/0181956 A1 | 9/2003 | Duncan et al. |
| 2004/0012470 A1 | 1/2004 | Zimmerling et al. |
| 2004/0059423 A1 | 3/2004 | Barnes et al. |
| 2004/0167450 A1* | 8/2004 | Buckman ............ A61F 5/0585 602/23 |
| 2004/0260361 A1 | 12/2004 | Gibson |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2005/0159791 A1 | 7/2005 | Daly et al. |
| 2005/0171579 A1 | 8/2005 | Tasche et al. |
| 2006/0030905 A1 | 2/2006 | Malaver |
| 2006/0184212 A1 | 8/2006 | Faltys et al. |
| 2006/0244560 A1 | 11/2006 | Zimmerling et al. |
| 2007/0126540 A1 | 6/2007 | Zimmerling |
| 2007/0208403 A1 | 9/2007 | Della Santina et al. |
| 2008/0221641 A1 | 9/2008 | Hochmair |
| 2009/0069869 A1 | 3/2009 | Stouffer et al. |
| 2009/0287278 A1 | 11/2009 | Charvin |
| 2011/0004278 A1 | 1/2011 | Aghassian |
| 2011/0022120 A1 | 1/2011 | Ball et al. |
| 2011/0264172 A1 | 10/2011 | Zimmerling et al. |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0172659 A1 | 7/2012 | Ball et al. |
| 2012/0238799 A1 | 9/2012 | Ball et al. |
| 2012/0296155 A1 | 11/2012 | Ball |
| 2012/0323066 A1 | 12/2012 | Cho et al. |
| 2012/0330378 A1 | 12/2012 | Crawford et al. |
| 2013/0046131 A1 | 2/2013 | Ball et al. |
| 2013/0046360 A1 | 2/2013 | Gibson et al. |

(56) References Cited

U.S. PATENT DOCUMENTS

| 2013/0053874 A1 | 2/2013 | Ekvall et al. |
| 2013/0110198 A1 | 5/2013 | Stoffaneller |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121447 A1 | 5/2014 | Kasic et al. |
| 2014/0213139 A1 | 7/2014 | Ferguson |
| 2014/0275736 A1 | 9/2014 | Ruppersberg et al. |
| 2014/0302741 A1 | 10/2014 | Whittaker |
| 2014/0343626 A1 | 11/2014 | Thenuwara et al. |
| 2015/0087892 A1 | 3/2015 | Tourrel et al. |
| 2015/0157778 A1 | 6/2015 | Ishiyama et al. |
| 2016/0008596 A1 | 1/2016 | Gibson et al. |
| 2016/0144170 A1 | 5/2016 | Gibson et al. |
| 2016/0361537 A1 | 12/2016 | Leigh et al. |

OTHER PUBLICATIONS

Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.
MED-EL, "Magnetic Resonance Imaging (MRI)," believed to be available in Jan. 2016.
D. Cuda et al., "Focused tight dressing does not prevent cochlear implant magnet migration under 1.5 Tesla MRI," believed to be available in Jan. 2016.

* cited by examiner

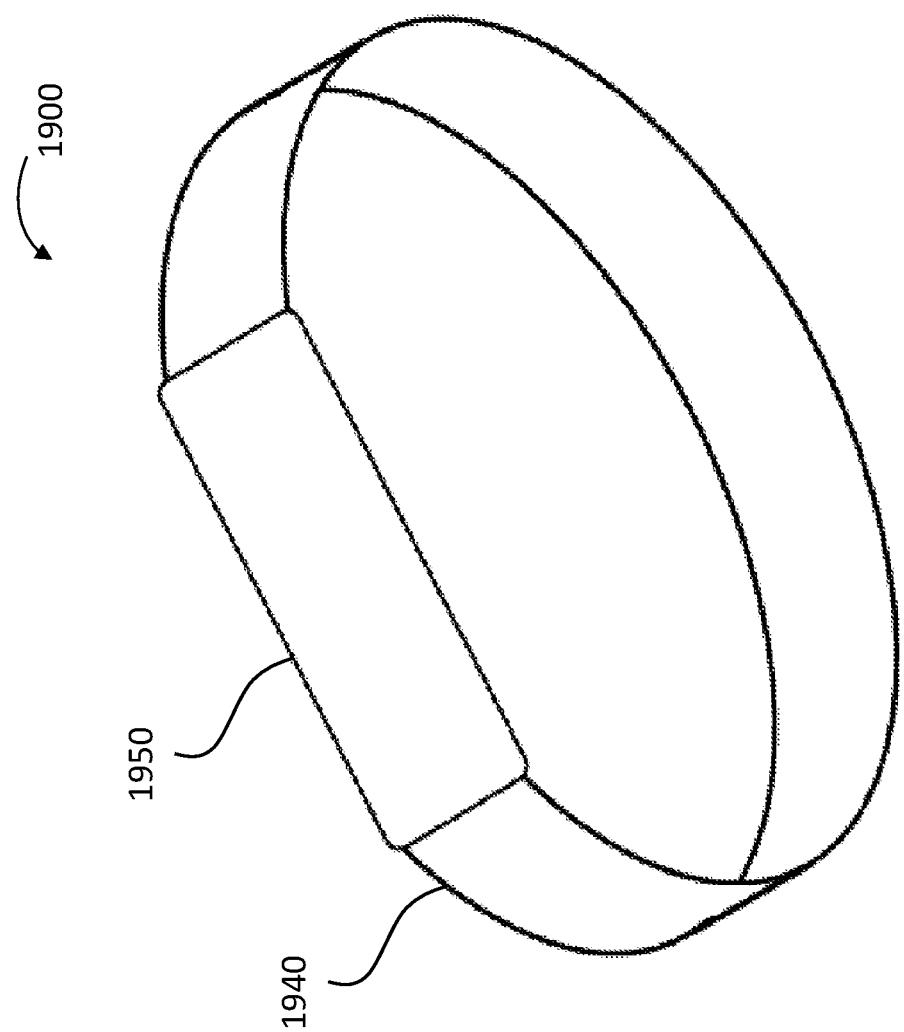

IMPLANTED MAGNET MANAGEMENT IN THE FACE OF EXTERNAL MAGNETIC FIELDS

CROSS-REFERENCE TO RELATED APPLICATIONS

This application claims priority to Provisional U.S. Patent Application No. 62/329,240, entitled IMPLANTED MAGNET MANAGEMENT IN THE FACE OF EXTERNAL MAGNETIC FIELDS, filed on Apr. 29, 2016, naming Charles Roger LEIGH of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is a method, comprising subjecting a subcutaneous medical device containing a magnet to a magnetic field, thereby imparting a torque onto the magnet, and resisting the imparted torque via an external device that has a skin facing component extending in a direction away from a curvature of the body of the recipient at locations proximate a portion directly contacting skin directly above the implanted magnet.

In accordance with another exemplary embodiment, there is a method comprising securing an MRI splint to a recipient such that a first force is applied against skin of the recipient at a location over a magnet implanted in the recipient, and subsequent to the action of securing, adjusting the MRI splint such that a second force is applied against the skin of the recipient at the location, the second force being different than the first force.

In accordance with another exemplary embodiment, there is an MRI splint assembly, comprising means for enhancing an interface with skin of the recipient at a location overlying an implanted magnet of an implantable component, and means for securing the means for enhancing an interface with skin of the recipient to the recipient, wherein the MRI splint assembly is configured to be secured to a head of the recipient.

BRIEF DESCRIPTION OF THE DRAWINGS

Embodiments are described below with reference to the attached drawings, in which:

FIG. 19 presents an exemplary MRI splint assembly according to an exemplary embodiment.

DETAILED DESCRIPTION

Exemplary embodiments will be described in terms of a cochlear implant. That said, it is noted that the teachings detailed herein and/or variations thereof can be utilized with other types of hearing prostheses, such as by way of example, bone conduction devices, DACI/DACS/middle ear implants, etc. Still further, it is noted that the teachings detailed herein and/or variations thereof can be utilized with other types of prostheses, such as pacemakers, muscle stimulators, etc. In some instances, the teachings detailed herein and/or variations thereof are applicable to any type of implanted component (herein referred to as a medical device) having a magnet that is implantable in a recipient.

Figure 1A:
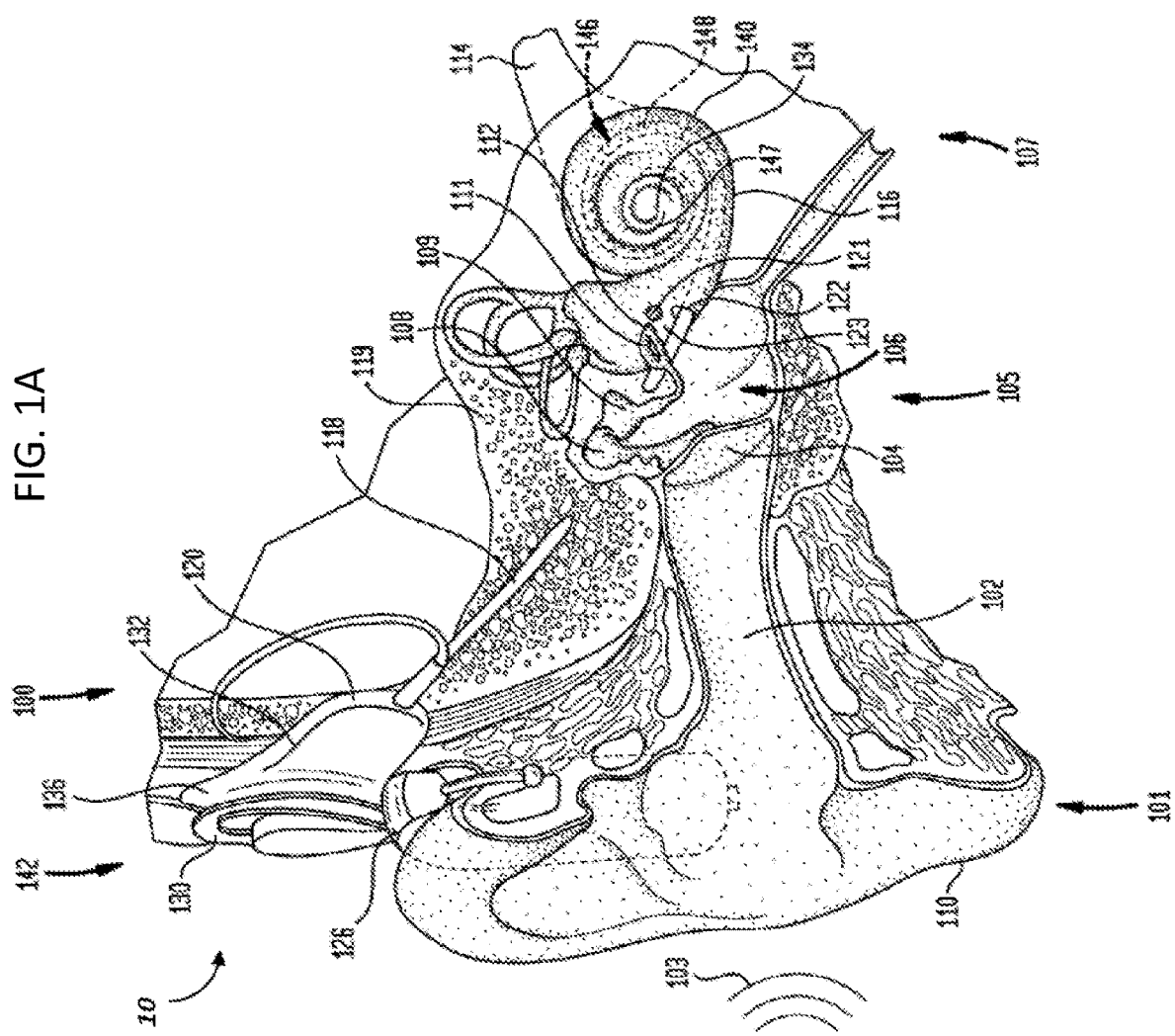
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prosthesis, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, and where the implanted cochlear implant includes a battery, that is recharged by the power provided from the external device 142.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil assembly 136. Internal coil assembly 136 typically includes a wire antenna coil comprised of multiple turns of electrically insulated single-strand or multi-strand platinum or gold wire, as will be described in greater detail below.

Cochlear implant 100 further comprises a main implantable component 120 and an elongate electrode assembly 118. Collectively, the coil assembly 136, the main implantable component 120, and the electrode assembly 118 correspond to the implantable component of the system 10.

In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone or via internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown in FIG. 1A) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
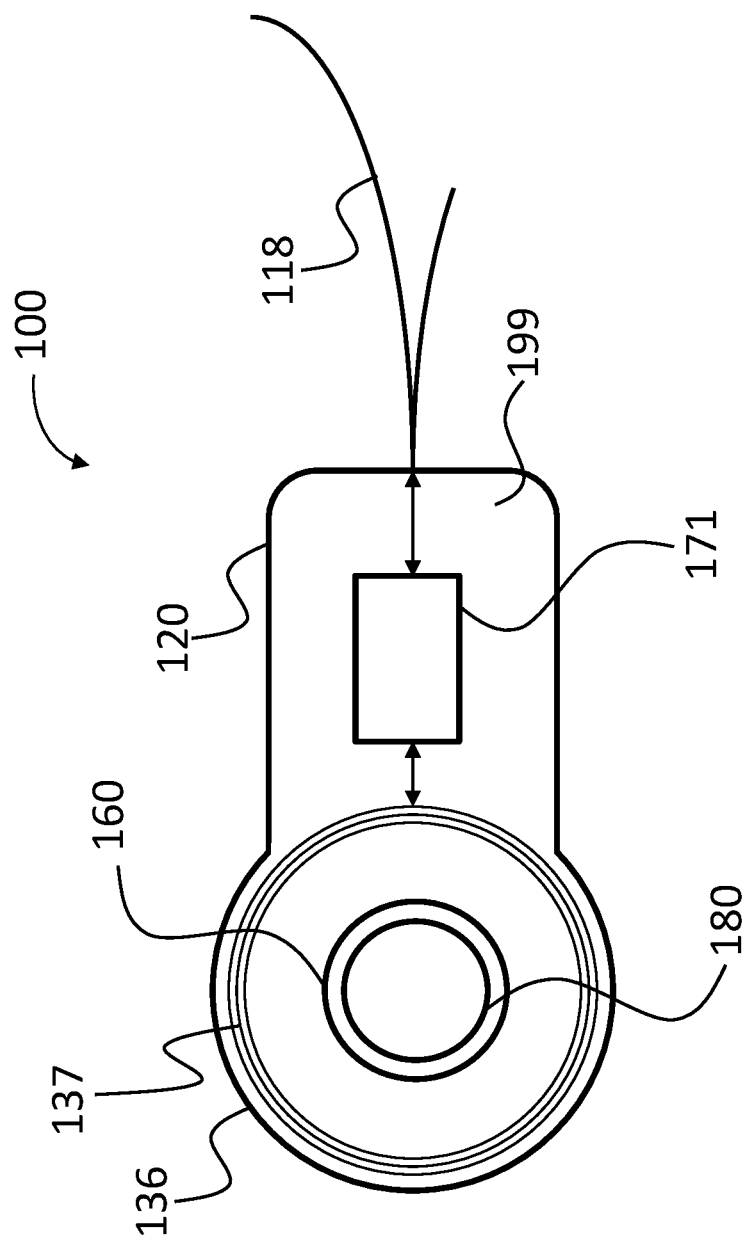
FIG. 1B is a top view of an exemplary hearing prosthesis in which at least some of the teachings detailed herein are applicable.

FIG. 1B depicts an exemplary high-level diagram of the implantable component 100 of the system 10, looking downward from outside the skull towards the skull. As can be seen, implantable component 100 includes a magnet 160 that is surrounded by a coil 137 that is in two-way communication (although in other embodiments, the communication is one-way) with a stimulator unit 171, which in turn is in communication with the electrode assembly 118.

Still with reference to FIG. 1B, it is noted that the stimulator unit 122, and the magnet apparatus 160 are located in a housing made of an elastomeric material 199, such as by way of example only and not by way of limitation, silicone. Hereinafter, the elastomeric material 199 of the housing will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

As can be seen in FIG. 1B, the housing made of elastomeric material 199 includes a hole 180 extending to the magnet apparatus 160. In an exemplary embodiment, the hole 180 has utilitarian value in that it can enable insertion and/or removal of the magnet apparatus 160 from the housing made of elastomeric material 199.

It is noted that magnet apparatus 160 is presented in a conceptual manner. In this regard, it is noted that in at least some embodiments, the magnet apparatus 160 is an assembly that includes a magnet surrounded by a biocompatible coating. Still further, in an exemplary embodiment, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container. Additional details of the container will be described below. In this regard, it is noted that sometimes the term magnet is used as shorthand for the phrase magnet apparatus, and thus any disclosure herein with respect to a magnet also corresponds to a disclosure of a magnet apparatus according to the aforementioned embodiments and/or variations thereof and/or any other configuration that can have utilitarian value according to the teachings detailed herein.

Figure 2:
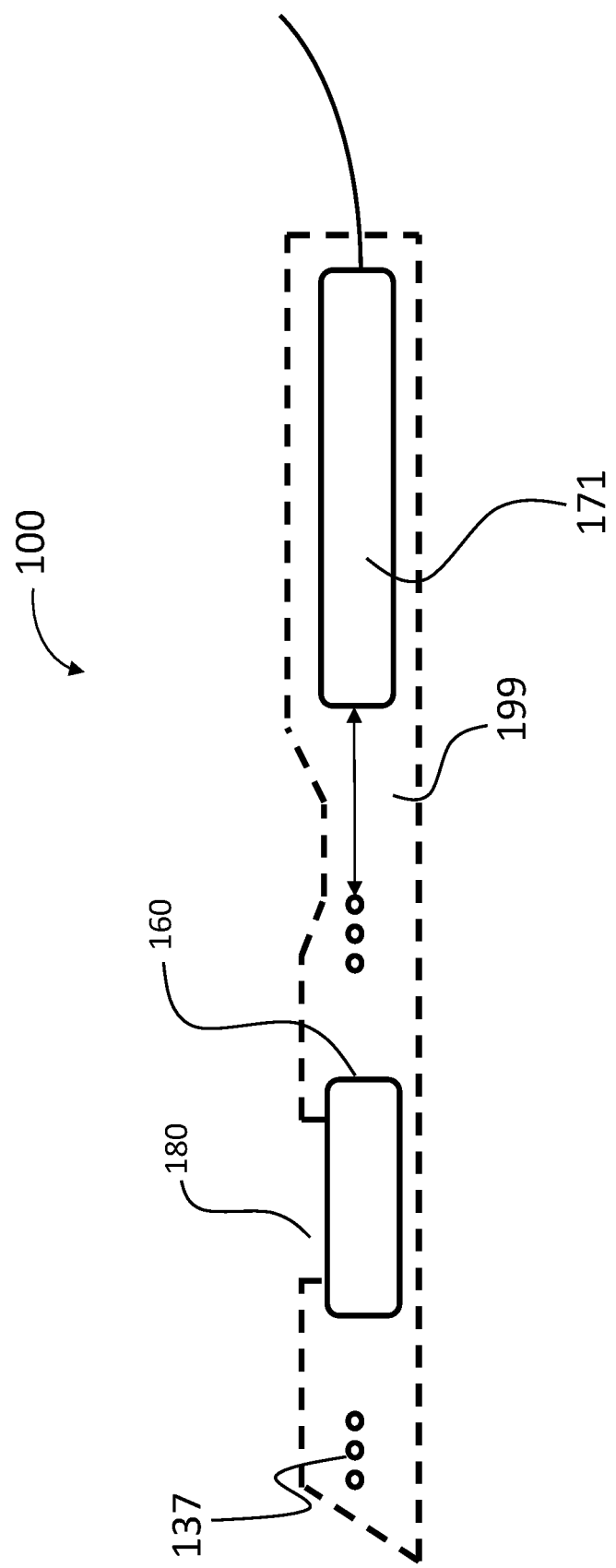
FIG. 2 is a side view of an exemplary hearing prosthesis in which at least some of the teachings detailed herein are applicable.

With reference now to FIG. 2, it is noted that the outlines of the housing made from elastomeric material 199 are presented in dashed line format for ease of discussion. In an exemplary embodiment, silicone or some other elastomeric material fills the interior within the dashed line, other than the other components of the implantable device (e.g., magnet, stimulator, etc.). That said, in an alternative embodiment, silicone or some other elastomeric material substantially fills the interior within the dashed lines other than the components of the implantable device (e.g., there can be pockets within the dashed line in which no components and no silicone is located).

It is noted that FIGS. 1B and 2 are conceptual FIGs. presented for purposes of discussion. Commercial embodiments corresponding to these FIGs. can be different from that depicted in the figures.

Figure 3:
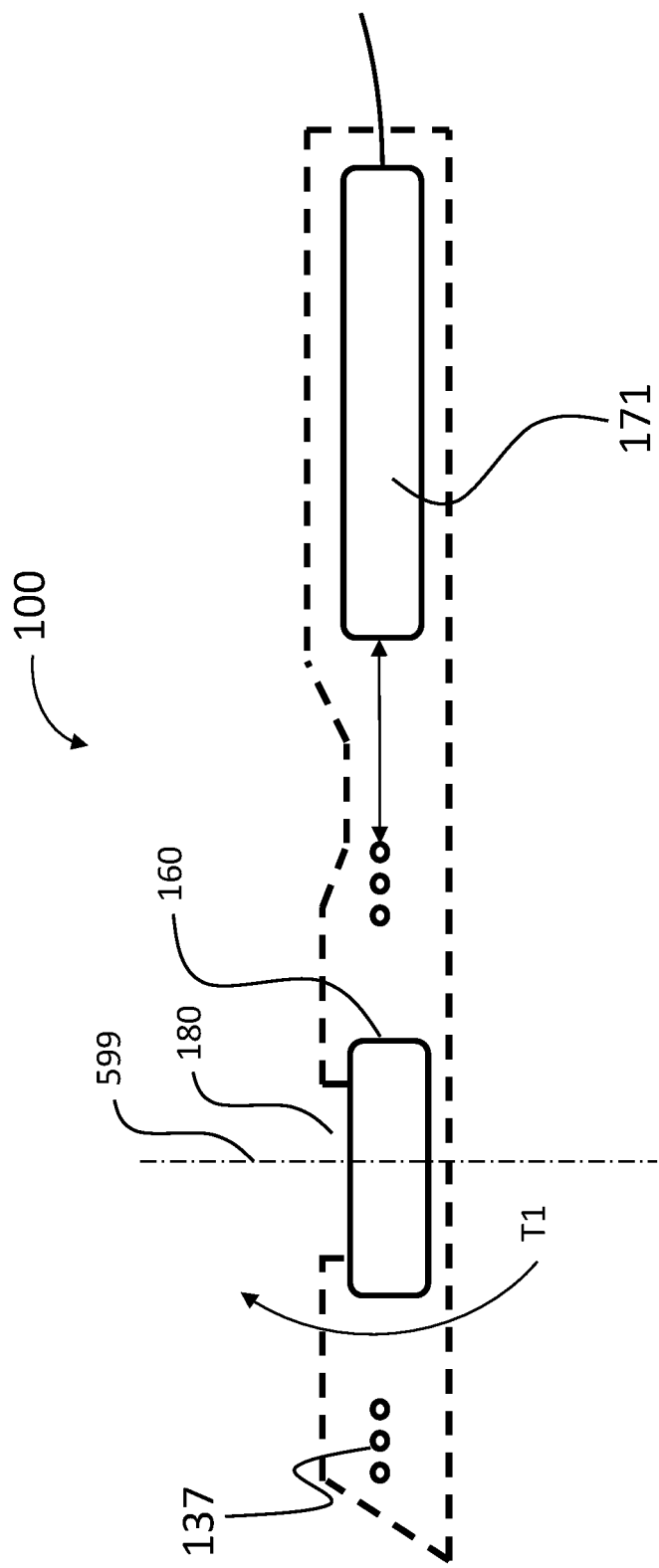
FIG. 3 is a reproduction of FIG. 2, except showing a functional representation of the application of a torque applied to the magnet 160.
Figure 4:
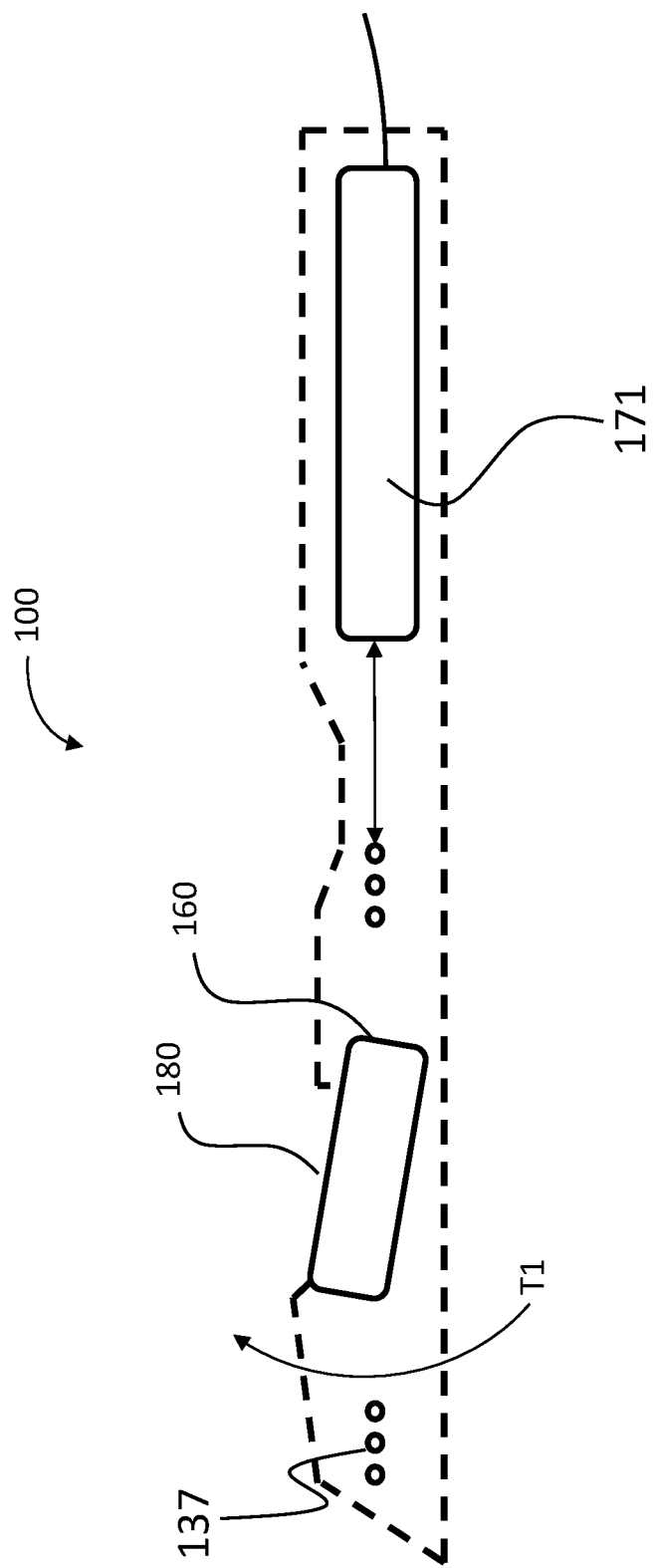
FIG. 4 depicts the exemplary hearing prosthesis of FIG. 2 where the torque applied to the magnet 160 has dislodged the magnet 160.

FIG. 3 depicts the implantable component 100 subjected to a magnetic field of an MRI machine. Specifically, FIG. 3 presents the magnet apparatus 160 of the implantable component 100 having a longitudinal axis 599. In this exemplary embodiment, the poles of the magnet of the magnet apparatus 160 are aligned with the axis 599. That is, in an embodiment where the magnet of the magnet apparatus 160 is a disk magnet (as is the case here), the poles are located on the flats. Thus, the magnet apparatus 160 has a north-south polar axis aligned with the longitudinal axis 599. As can be seen from FIG. 3, the magnetic field of the MRI machine imparts a torque, represented by arrow T1, on to the magnet apparatus 160. In a scenario where the magnetic field is strong enough, and the magnetic field is angled relative to the longitudinal axis 599 in a certain way, the torque T1 can be sufficiently strong enough so as to dislodge the magnet apparatus 160 from the pockets inside the housing 199 established by the silicon. This is functionally represented by FIG. 4, which depicts magnet 160 in a semi-dislodged state such that the silicone of the housing 199 has been deformed (permanently or non-permanently) relative to that which was the case prior to subjecting the magnet apparatus 162 the MRI magnetic field.

As noted above, the magnet apparatus of the implantable component 100 is a disk magnet apparatus/has the form of a short cylinder. That said, in an alternative embodiment, the magnets can have another configuration (e.g., a plate magnet, a bar magnet, etc.) or can be magnetically polarized in a different plane (e.g., a diametrically polarized magnet has a polar axis that is aligned with the diameter of a disc magnet, the width of a plate magnet, or the length of a bar magnet). Moreover, in an alternative embodiment, two or more magnets can be used in the implantable device and/or in the external device. The magnets could be located outboard of the coil. Any arrangement of magnet(s) of any configuration that can have utilitarian value according to the teachings detailed herein and/or variations thereof can be utilized in at least some implantable components. In any event, in at least some scenarios, a sufficiently strong magnetic field at the "correct" angle relative to the magnetic poles of the magnet of the magnet apparatus can result in dislodgment of the magnet apparatus (which encompasses complete removal of the magnet from the pocket in the implantable component 100, and the dislodgment depicted in FIG. 4H, etc.). There is utilitarian value with respect to applying a counterforce over the skin of the recipient to counteract the torque T1 that results from the magnetic field so as to avoid the dislodgment and/or discomfort to the recipient.

Figure 5:
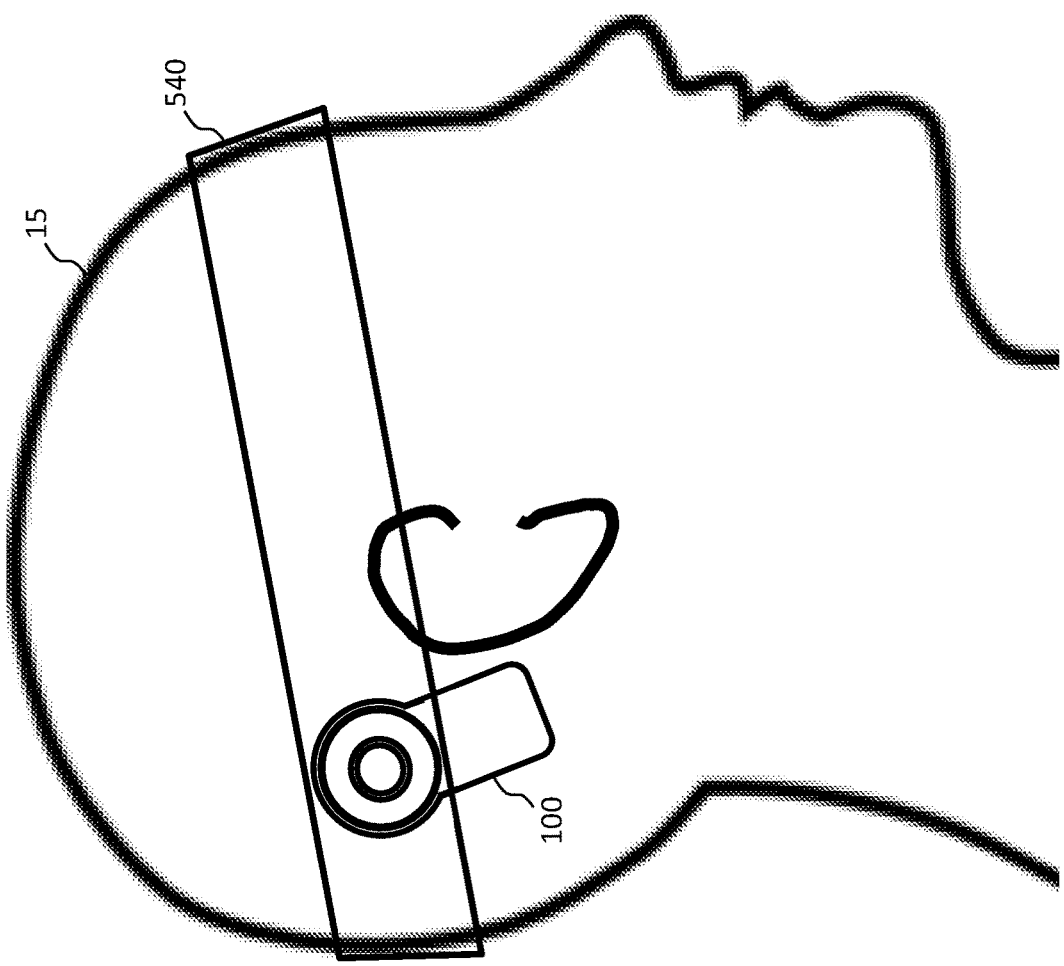
FIG. 5 depicts an exemplary belt utilized to apply force to skin over the implanted magnet.

FIG. 5 depicts a side view of a human head 15 having implanted therein the implantable component 100. In an exemplary embodiment, a belt 540 extends about the head of the recipient. The belt 540 applies a compressive force over the skin of the recipient over the magnet apparatus 160 so as to counteract the torque T1 that results from the magnetic field. In an exemplary embodiment, the belt 540 can be bandage material wrapped around the head of the recipient in a manner concomitant with standard bandaging techniques. In some embodiments, the belt 540 can be nylon webbing or leather, and can have a buckle type apparatus to maintain tension on the material (or the material can be potentially tied off like one would do with the bandage material, or the material could be safety clipped (e.g., using a plastic safety pin), also like one could do with the bandage material. Any suitable biocompatible material that will not interfere with the magnetic field produced by the MRI machine can be utilized as the belt 540.

Figure 6:
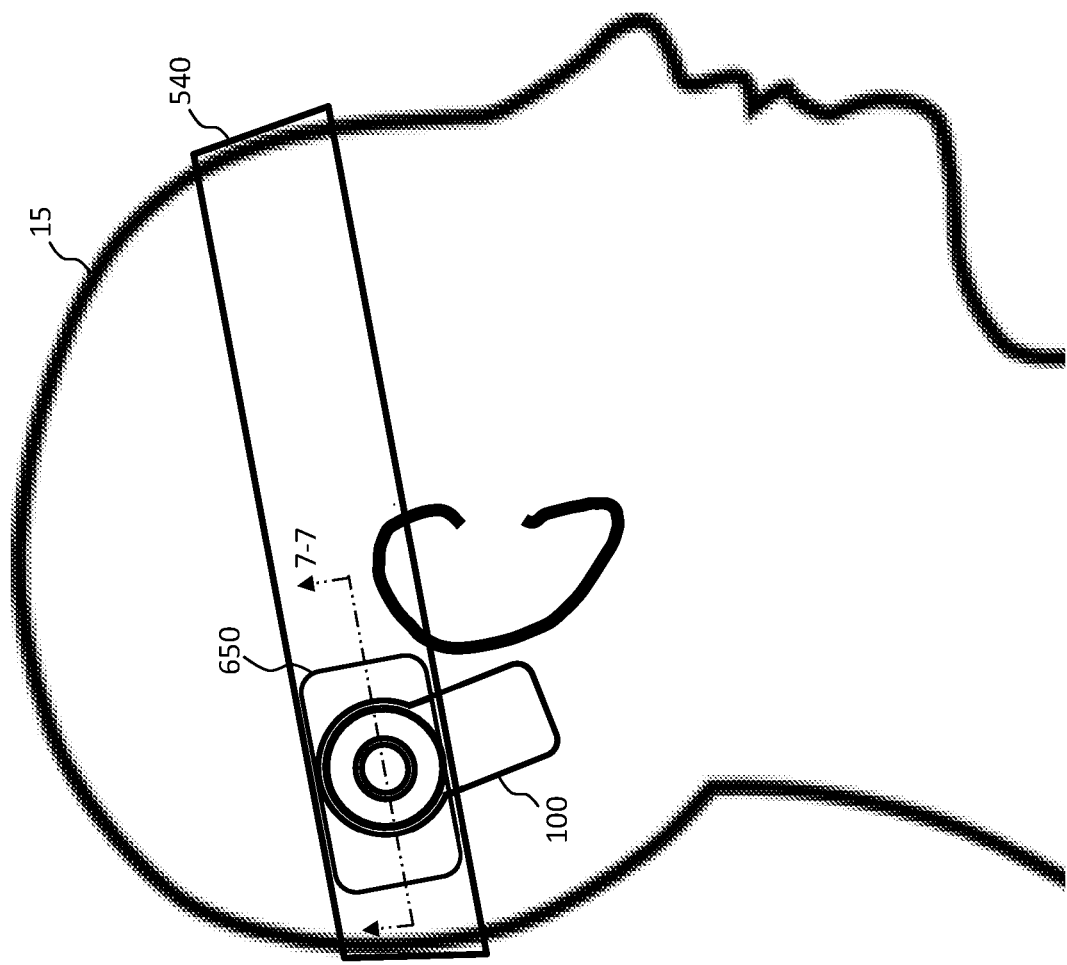
FIG. 6 depicts an exemplary MRI splint assembly utilizing the belts of FIG. 5.
Figure 7:
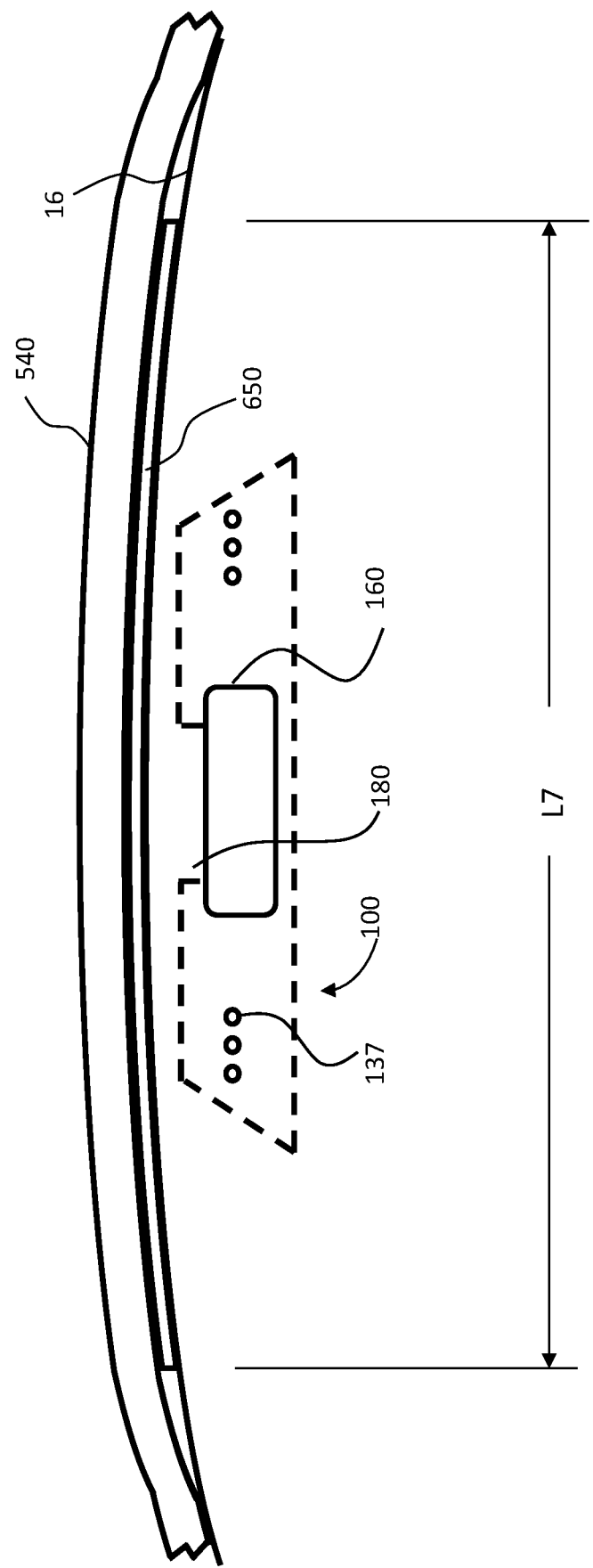
FIG. 7 depicts a cross-sectional view of a portion of the MRI splint assembly of FIG. 6.

FIGS. 6 and 7 depict an assembly that includes a belt 540 and a splint 650. In an exemplary embodiment, splint 650 is configured to contour to the outer skin of the recipient upon the application of sufficient attention to the belt 540 so that the splint 650 is pressed against the skin of the recipient, thus applying a force on the skin over the location of the magnet apparatus 160. FIG. 6 depicts the view of FIG. 5, and FIG. 7 depicts a cross-sectional view therethrough. As can be seen, the splint 650 is uniformly pressed against the outer surface 16 of the recipient 16 by the belt 540 (where, of course, hair could be located between the splint 650 and the skin of the recipient—in this regard, the scenario where hair is located between the splint and the skin of the recipient results in the splint being effectively in contact with the skin of the recipient). In an exemplary embodiment, the splint 650 provides a surface that is less deformable in the direction normal to the tangent surface of the skin over the magnet than that which is the case with respect to the material of the belt 540. For example, in the case of bandage material, the bandage material is still sufficiently flexible that a force applied to the material will cause the material to deform. In the case where a localized force is produced by movement of the magnet owing to the torque applied thereto by the magnetic field to the MRI, the material will deform by at least a certain amount, which may not be enough to provide a sufficient counterforce over the skin of the recipient to prevent the magnet from becoming dislodged. The splint 650 provides a less deformable surface, thus mitigating at least in part the localized deformation of the belt that would otherwise result. In an exemplary embodiment, the splint 650 is made of ABS plastic.

Figure 8:
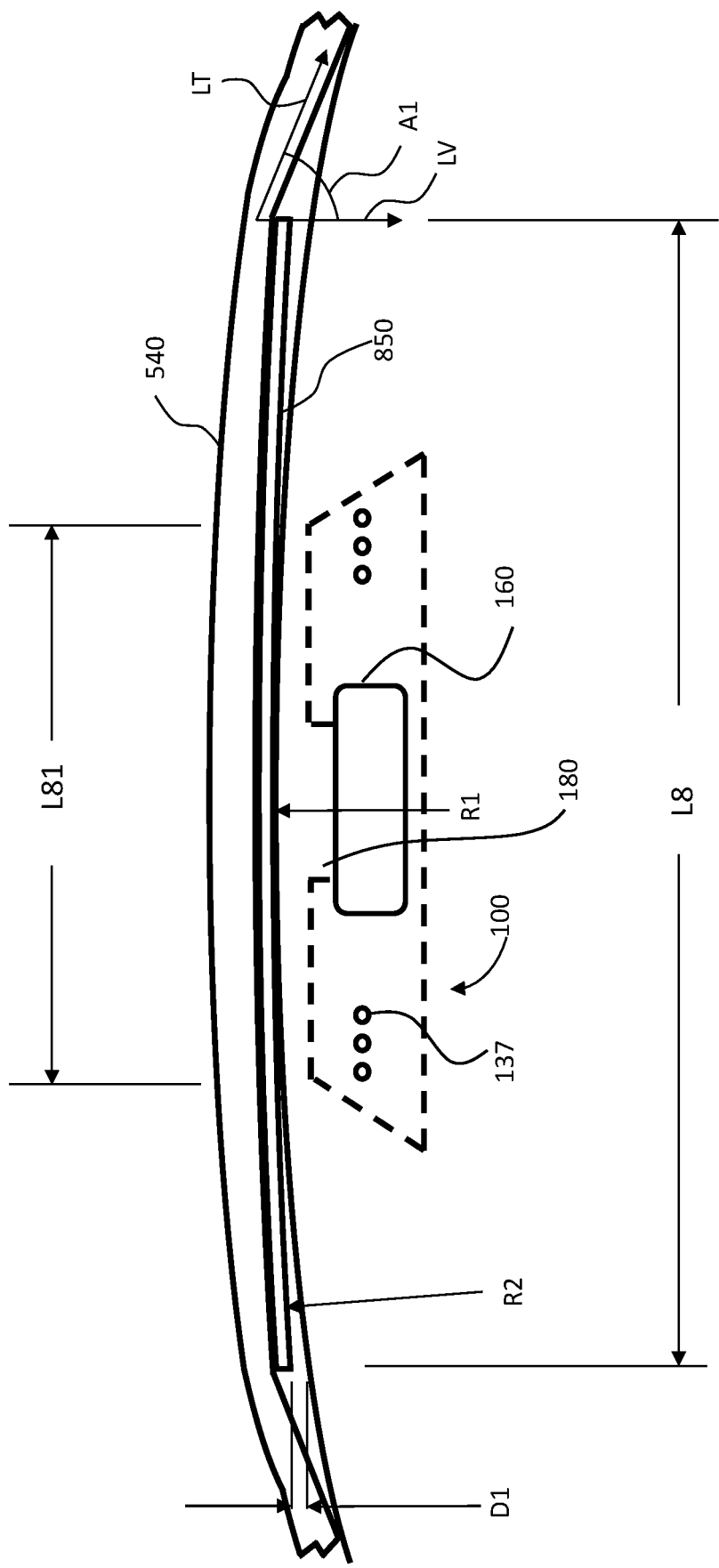
FIG. 8 depicts an enhanced MRI splint assembly according to an exemplary embodiment.

FIG. 8 depicts an exemplary embodiment of an enhanced splint 850. Here, the splint is more rigid than the splint of the embodiment of FIGS. 6 and 7, and thus the splint 850 is only partially contoured to the outside of the recipient. As can be seen, the ends of the splint 850/the locations at the outer perimeter of the splint 850 are raised above the skin of the recipient by a distance D1 on at least one side. In an exemplary embodiment, the locations of the outer perimeter of the splint 850 are raised above the skin of the recipient by a distance that is the same on both sides, while in other embodiments, the locations of the outer perimeter of the splint 850 are raised above the skin of the recipient by distances that are different on both sides. In an exemplary embodiment, the distance(s) D1 are about 1 mm to 15 mm or any value or range of values therebetween in about 0.1 mm (e.g., about 2 mm, about 3, mm, about 4 mm, about 8 mm about 12, mm, etc.).

With respect to the embodiments of FIGS. 6, 7, and 8, the belt 540 is tensioned to the same amount. In this regard, it is noted that standard practices with respect to the medical profession, medical regulations, or otherwise typical efforts to treat people humanely, result in limitations with respect to the amount of tension that can be applied to the belt 540. Indeed, in practice, the limit is often a practical one of simply how much tension can the person applying the bandage maintain while they wrap tape around the head to hold the belt (e.g., bandage) in place. This is in conflict somewhat with the fact that the more tension that is applied to the belt, the more compressive force applied onto skin over the magnet of the implantable component will result, and thus the greater resistance to the torque applied to the magnet by the MRI magnetic field. The increase in force countering the torque depends on, for example, the component of force acting normal to the head surface. As explained later, this force will depend on the angle A1 (of FIG. 7) which in turn depends on the curvature of the head. For a large radius of curvature, the angle A1 is near 90 degrees. This means that the component of force normal to the head surface can be very small even for a relatively high tension. Even assuming arguendo a scenario where a recipient was sufficiently drugged so as to not feel the discomfort or pain from a high tensioned belt, high tensioned belts 540 could result in a tourniquet functionality. Recognizing that MRI procedures can last many hours, it may not be optimal to cut off or otherwise restrict the flow of blood within the head for such a lengthy period of time.

The fact that the enhanced splint 850 avoids total conformity to the outer skin of the recipient means that the belt 540 is angled by an amount A1 at the locations where the belt 540 crosses the perimeter of the enhanced splint 750 that is less than the amount that is the case for the splint 650. This has the effect of increasing the downward force applied to the skin of the recipient, all other things being equal (e.g., for the same amount of tension in the belt 540). That is, with respect to the legs of the vertices forming the angle A1, where LV is the leg in the vertical direction, and LT is the leg in the tensile direction (the direction of extension of belt 540 at the perimeter of the splint 750), the less of an angle A1 between LT and LV, the greater LV, and thus the greater the compressive force on the skin of the recipient for a given tension (e.g., the force in the direction of the leg LT), all other things being equal.

In an exemplary embodiment, the force LV is increased by at least 5%, 6%, 7%, 8%, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 160, 170, 180, 190, 200, 225, 250, 275, or 300%, or more, or any value or range of values therebetween in 0.1% increments (e.g., 5.5% greater, 33.33% greater, 8.2% to 22.2% greater, etc.) due to the fact that the perimeter of the enhanced splint 850 is uplifted away from the skin of the recipient relative to that which would be the case if the perimeter of the enhanced splint 850 was not so uplifted, all other things being equal (e.g., the tension LT being the same, etc.).

In an exemplary embodiment, the angle A1 is reduced by at least about 1%, 2%, 3%, 4%, 5%, 6%, 7%, 8%, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or about 40%, or more, or any value or range of values therebetween in 0.1% increments due to the fact that the perimeter of the enhanced splint 850 is uplifted away from the skin of the recipient relative to that which would be the case if the perimeter of the enhanced splint 850 was not so uplifted, all other things being equal (e.g., the tension LT being the same, etc.).

Accordingly, in an exemplary embodiment, there is an MRI splint configured such that a lashing angle of the belt (i.e., angle A1) is reduced relative to that which would be the case for the embodiment of FIG. 6.

In an exemplary embodiment, the aforementioned angles are achieved by utilizing a splint 850 that is more rigid than the splint 650 detailed above, thus making the splint 850 an enhanced splint. In an exemplary embodiment, the enhancement results from making the splint 850 thicker relative to that of splint 650, all other things being equal. By way of example only and not by way of limitation, in an exemplary embodiment, the splint 650 corresponds to a splint that meets the requirements of ISO/IEC 7810 as of Apr. 17, 2016, for an identification card that is an ID-1 identification card per that specification. In an exemplary embodiment, the splint 650 corresponds to a splint having a length that is 85.60 mm (corresponding to L8 of FIG. 8 when splint 850 is perfectly flat—that is, the dimension L8 of FIG. 8 is not to the edges of the splint as flexed in the figure, but to the edges of the splint in the perfectly flat regime (not shown in the FIG.), a width corresponding to 53.98 mm, and a thickness of 0.76 mm. Conversely, the enhanced splint 850 is made from the exact same material and has the same length and the same width, but the thickness is increased by about 40% or more (e.g., the thickness is about 1.1 mm or more). In an exemplary embodiment, the enhancement to the splint 650 corresponds to increasing the thickness of the splint 650 by about 33%, about 34%, 35%, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 145, 150, 160, 170, 180, 190, 200, 210, 220, 230, 240, 250%, or more, or any value or range of values therebetween in about 0.1% increments to achieve splint 850. Thus, in an exemplary embodiment, the splint 850 can be a splint that meets all of the requirements of the ISO standard but for the thickness (and thus the rigidity, more on this below), where the thickness is about 1.0 mm, 1.01 mm, 1.02 mm, 1.03 mm, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.4, 1.45, 1.5, 1.55, 1.6, 1.65, 1.7, 1.75, 1.8, 1.85, 1.9, 1.95, or 2 mm, or more, or any value or range of values therebetween in about 0.005 mm increments.

In an exemplary embodiment, the splints 650 and 850 are a solid piece of ABS plastic. In an exemplary embodiment, at least about 90% of the splint by weight is made of ABS plastic. In an exemplary embodiment, at least about 91%, 92%, 93%, 94%, 95%, 96%, 97%, 98%, 99%, or 100%, of the splint by weight is made of ABS plastic. As noted above, splint 650 corresponds to a splint that meets the requirements of ISO/IEC 7810 as of Apr. 17, 2016, for an identification card that is an ID-1 identification card per that specification. That means it has a given rigidity per that standard. Conversely, the enhanced splint has a rigidity that is greater than that of the splint 650. In an exemplary embodiment, all other things being equal, the splint 850 is 33%, about 34%, 35%, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 145, 150, 160, 170, 180, 190, 200, 210, 220, 230, 240, 250%, or more rigid, or any value or range of values therebetween in about 0.1% increments than the splint 650. That said, in an alternative embodiment, all other things are not equal, and thus the thickness is increased relative to that which is the case for the splint 650 according to the aforementioned ISO standard. Accordingly, in an exemplary embodiment, there is a splint where the thickness is increased to achieve the aforementioned enhanced rigidities. It is noted that the above increases in rigidity and thickness could be achieved by using two or more splints in a stack. That is, in an exemplary embodiment, the splint 850 could comprise two or more separate splint components layered on top of each other. Any arrangement that can achieve the teachings detailed herein can be used to practice some embodiments.

As noted above, in an exemplary embodiment, the splint 650 has a rigidity such that for a given tension on the belt 540 (e.g., a tension LT), the perimeter of the splint 650 will be pressed by the belt 540 against the skin of the recipient (albeit hair will be located in between the bottom surface of the splint 650 and the skin). In an exemplary embodiment, for a 50 percentile human factors male resident of the United States of America as of Apr. 17, 2016, of age 60 years, having a cochlear implant where the magnet is implanted above the mastoid bone of the recipient, using a standard surgical bandage webbing, the tension LT that will just force the perimeter of the splint 650 down to contact the skin of the recipient is LTT (LT threshold). In an exemplary embodiment, for a 50 percentile human factors male resident of the United States of America as of Apr. 17, 2016, of age 60 years, having a cochlear implant where the magnet is implanted above the mastoid bone of the recipient, using a standard surgical bandage webbing, the tension LT that will force the perimeter of the splint 650 down to contact the skin of the recipient that cannot be increased without causing a synergistic deleterious effect if left at that tension for 1 hour or more is LTA (LT absolute). In an exemplary embodiment, the enhanced splint 850 is configured such that for a belt tensioned to LTT, all other things being equal with respect to the splint 650 save for the rigidity, the perimeter of the splint 850 will be at at least one of the aforementioned distances D1. In an exemplary embodiment, the enhanced splint 850 is configured such that for a belt tensioned to LTA, all other things being equal with respect to the splint 650 save for the rigidity, the perimeter of the splint 850 will be at at least one of the aforementioned distances D1.

It is noted that while the embodiments detailed above have been presented in terms of increasing the thickness, and thus the rigidity, of the splint 650 to achieve the enhanced splint 850, it is noted that there can be utilitarian value with respect to limiting the rigidity of the splint 850. By way of example only and not by way of limitation, because the process by which the splint 850 is centered over the magnet is not foolproof (e.g., because the magnet cannot be seen as it is implanted underneath the skin of the recipient, although owing to the innovative efforts associated with the inventors of this application, that too has been remedied at least in part as detailed below), there is utilitarian value with respect to having some amount of flexibility of the splint. In this regard, a splint that has some flexibility will result in the locations proximate the center of the splint still contacting the skin of the recipient. By way of example only and not by way of limitation, with respect to the aforementioned enhanced splint 850, the splint 850 will contact the skin of the recipient/provide compressive force onto the skin of the recipient over a distance corresponding to L81, where L81 is about centered with the middle of splint 850. Thus, in at least some exemplary embodiments, providing that the magnet 160 is located within the "borders" of L81, there will be a compressive force that results on to the skin of the recipient, thus, providing the counterforce against the torque applied to the magnet by the MRI magnetic field. Accordingly, in an exemplary embodiment, there is a splint that has a rigidity such that for a given tension LT, about half of the length of the splint will provide compressive force onto skin of the recipient, and about half of the length of the splint will not provide compressive force onto the skin of the recipient, all other things being equal. That given tension LT can be the tension LTT or LTA or any appropriate tension.

Thus, there is utilitarian value with respect to controlling the rigidity or thickness of the enhanced splint. In an exemplary embodiment, the enhancement to the splint 650 corresponds to increasing the thickness of the splint 650 by no more than about 33%, about 34%, 35%, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 145, 150, 160, 170, 180, 190, 200, 210, 220, 230, 240, 250%, or any value or range of values therebetween in about 0.1% increments to achieve splint 850. Thus, in an exemplary embodiment, the splint 850 can be a splint that meets all of the requirements of the ISO standard but for the thickness (and thus the rigidity, more on this below), where the thickness is no more than about 1.0 mm, 1.01 mm, 1.02 mm, 1.03 mm, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.4, 1.45, 1.5, 1.55, 1.6, 1.65, 1.7, 1.75, 1.8, 1.85, 1.9, 1.95, or 2 mm or any value or range of values therebetween in about 0.005 mm increments. In an exemplary embodiment, the splint 850 is no more than about 33%, about 34%, 35%, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 145, 150, 160, 170, 180, 190, 200, 210, 220, 230, 240, 250% more rigid, or any value or range of values therebetween in about 0.1% increments than the splint 650.

In an exemplary embodiment, the rigidity of the splint 850 is about 0.05 Nm, 0.075 Nm, 0.1 Nm, 0.125 Nm, 0.15 Nm, 0.175, 0.2, 0.225, 0.25, 0.275, 0.3, 0.325, 0.35, 0.375, 0.4, 0.425, 0.45, 0.475, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 or 2.5 Nm or any value or range of values therebetween in 0.005 Nm increments, wherein the rigidity of the plate is calculated using the following equation:

$$D = \frac{Eh^3}{12(1-v^2)}$$

Where h is the thickness of the plate (or the height of the plate), E is the Young's Modulus and v is the Poisson's ratio. In an exemplary embodiment, the thickness can vary from 0.5 mm to 2 mm, and so the flexural rigidity can vary from about 0.03 Nm to about 1.9 Nm.

Accordingly, it is to be understood that some exemplary embodiments include a splint that is more rigid than the embodiment of FIG. 6, but which is not a completely rigid component. In this regard, the splint can be considered a semi-flexible component. Thus, by fixing an external device, such as a semiflexible splint 850 to the head of the recipient via a tension system (e.g., surgical bandage, etc.), wherein the semi-flexible component resists complete conformation with the head of the recipient when the full amount of tension is applied to the tension system, which full amount of tension is used while subjecting the subcutaneous medical device containing the magnet to the magnetic field, a margin of error can be factored into any method detailed herein.

It is noted that the aforementioned lengths and widths of the splint 650 and 850 are exemplary. In an exemplary embodiment, the length could be about 75 mm, 76 mm, 77, 78, 79, 80, 81, 82, 83, 84, 85, 86, 87, 88, 89, 90, 91, 92, 93, 94, or about 95 mm, or any value or range of values therebetween in 0.1 mm increments. In an exemplary embodiment, the width could be about 25 mm, 26 mm, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 75, 80, 85, 90, 95, 100, 105, 110, 115, 120, 125, 130 mm or more, or any value or range of values therebetween in 0.1 mm increments. (It is further noted that these values can correspond to the length as well.) Any dimensions that can have utilitarian value with respect to implementing the teachings detailed herein and/or variations thereof can be utilized in at least some exemplary embodiments. It is further noted that with respect to achieving the features associated with D1 (i.e., having at least a portion of the perimeter of the splint 850 uplifted from the skin of the recipient), there will be interplay with respect to, for example, the length, the thickness, and the material properties (e.g., utilizing a material that has a different molecular/unit value rigidity than that of ABS plastic for example) will combine to influence the aforementioned uplifting. Accordingly, embodiments can include any adjustments and variations in the length, width, and thickness, and material properties that can enable the enhancements detailed herein and/or variations thereof.

Thus, it can be seen that some embodiments include an MRI splint assembly including a splint 850 and a belt 540. The splint 850 can be a rectangular component that has a length, width, and a thickness, the length and width forming the rectangular feature (note that while in some embodiments the edges of the rectangular portion are rounded, as can be seen in the FIGs., this still represents a rectangular component). In some exemplary embodiments, the thickness is at least an order of magnitude less than the length and/or the width, and the thickness is at least one (1) mm. In an exemplary embodiment, the thickness is at least about two orders of magnitude less than the length and/or the width, and the thickness is at least 1 mm. In an exemplary embodiment, the splint 850 has a thickness to length aspect ratio of at least 0.01. In an exemplary embodiment, the thickness to length aspect ratio is at least or is about 0.01, 0.011, 0.012, 0.013, 0.014, 0.015, 0.016, 0.016, 0.017, 0.018, 0.019, 0.02, 0.021, 0.022, 0.023, 0.024, 0.025, 0.026, 0.027, 0.028, 0.029, 0.030, 0.032, 0.034, 0.036, 0.038, 0.04, 0.045, 0.05, 0.055, 0.06, 0.07, 0.08, 0.09 or 0.10 or any value or range of values therebetween in 0.001 increments. In an exemplary embodiment, the splint 850 has a thickness to width aspect ratio of at least or about any of the aforementioned values with respect to the thickness to length aspect ratio. In an exemplary embodiment, the aforementioned thicknesses are constant over the length and/or over the width. That said, in an exemplary embodiment, the thicknesses can vary over the length and/or over the width by an amount beyond that which is a result of general tolerancing such as by way of example only and not by way of limitation, about 5%, 10%, 15%, 20%, 25%, 30%, or any value or range of values therebetween in 1% increments.

Still with reference to FIG. 8, it can be seen that the enhancements associated with the splint 850 can be described in terms of having a splint that, for a given tension on the belt 540, has a different radius of curvature than that of the local skin of the recipient (e.g., the area of the skin proximate the area over the magnet. In an exemplary embodiment, the radius of curvature R2 of the splint 850 when a given tension is applied is about 10% greater than the local radius of curvature R1 of the skin (e.g., the radius of curvature of the skin directly beneath/eclipsed by the splint 850. In an exemplary embodiment, R2 is about 0.5%, 0.6%, 0.7, 0.8, 0.9, 1.0, 1.1, 1.2, 1.3, 1.4, 1.5, 1.6, 1.7, 1.8, and 1.9, 2.0, 2.25, 2.5, 2.75, 3.0, 3.25, 3.5, 3.75, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%, or more than R1 or any value or range of values therebetween in 0.1% increments.

Figure 9:
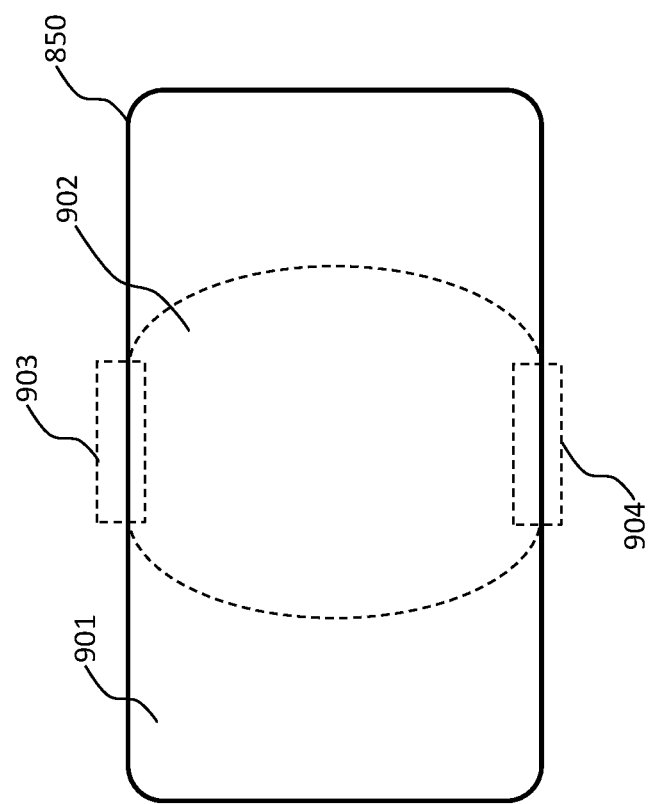
FIG. 9 depicts an exemplary zone of skin contact according to an exemplary splint according to an exemplary embodiment.
Figure 10:
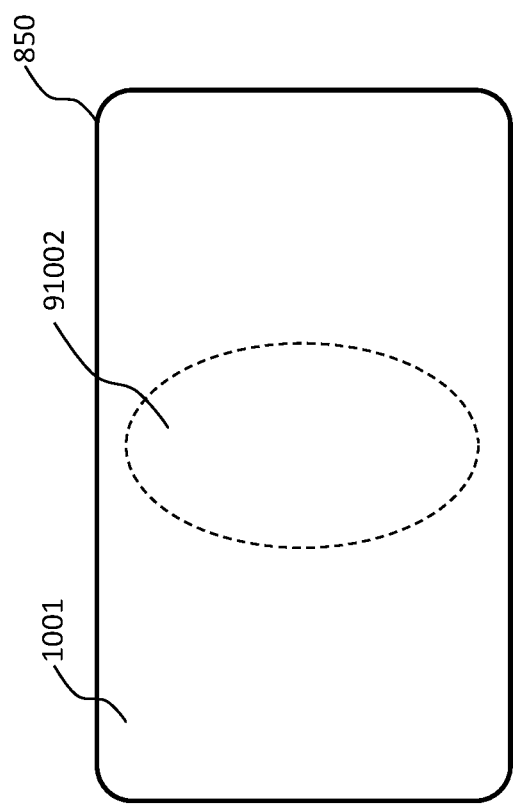
FIG. 10 depicts another exemplary zone of skin contact according to an exemplary splint according to an exemplary embodiment.

It is also noted that due to the fact that the width of the splint 850 is less than that of the length, in an exemplary embodiment, the aforementioned uplifting features may not necessarily be present at the perimeters associated with the width. More accurately, in an exemplary embodiment, with respect to the rectangular shape when viewed from the view of FIG. 6, the portions of the splint establishing the perimeter along the length dimension will be uplifted away from the skin, but the portions of the splint establishing the perimeter along the width dimension will not all be uplifted from the skin (or, more accurately, may not all be uplifted from the skin). In this regard, owing to the fact that the width of the splint is less than the length, the perimeter in the width direction closest to the geometric center of the splint may be in direct contact with the skin of the recipient. FIG. 9 depicts an exemplary view of an exemplary embodiment where portions of the splint 850 may not be in contact with the skin of the recipient and where portions of the splint 850 may be in contact with the skin of the recipient. In particular, the areas inside the dashed curve 902, and thus the portions of the perimeter within the dashed boxes 903 and 904, will come into contact with skin of the recipient (albeit through the hair)/will apply pressure to skin of the recipient, and the areas outside the dashed curve 904, and thus the portions of the perimeter outside the dashed boxes 903 and 904, do not come into contact with skin of the recipient/will not apply pressure to skin of the recipient. That said, an alternative embodiment can be practiced such that no portion of the perimeter of the splint 850 comes in to contact with skin of the recipient, such as that seen in FIG. 10 where the portions inside the dashed curve 1002 come into contact with skin of the recipient/apply pressure to the skin of the recipient, and the portions outside the dashed curve 1001 do not come into contact with skin of the recipient/do not apply pressure to the skin of the recipient.

Thus, there exists an MRI splint, comprising a means for enhancing an interface with skin of the recipient (e.g., the enhanced splint 850) and a means for securing the means for interfacing with skin of the recipient to the recipient (e.g., surgical bandage (which includes surgical gauze)) wherein the MRI splint is configured to be secured to a head of the recipient. Note that this is distinguished from the non-enhanced interface, such as the embodiment of FIG. 6.

In view of the above, the means for enhancing interface is configured to flex, and the MM splint is configured such that the means for securing is tensionable, thus causing the means for interfacing to flex towards the head of the recipient upon tensioning. In this exemplary embodiment, the means for enhancing the interface is configured to flex to have a radius of curvature that is greater than a localized radius of curvature of skin of the recipient at the location where the means for enhancing the interface with skin of the recipient interfaces with skin of the recipient upon tensioning of the means for securing to a point.

Figure 11:
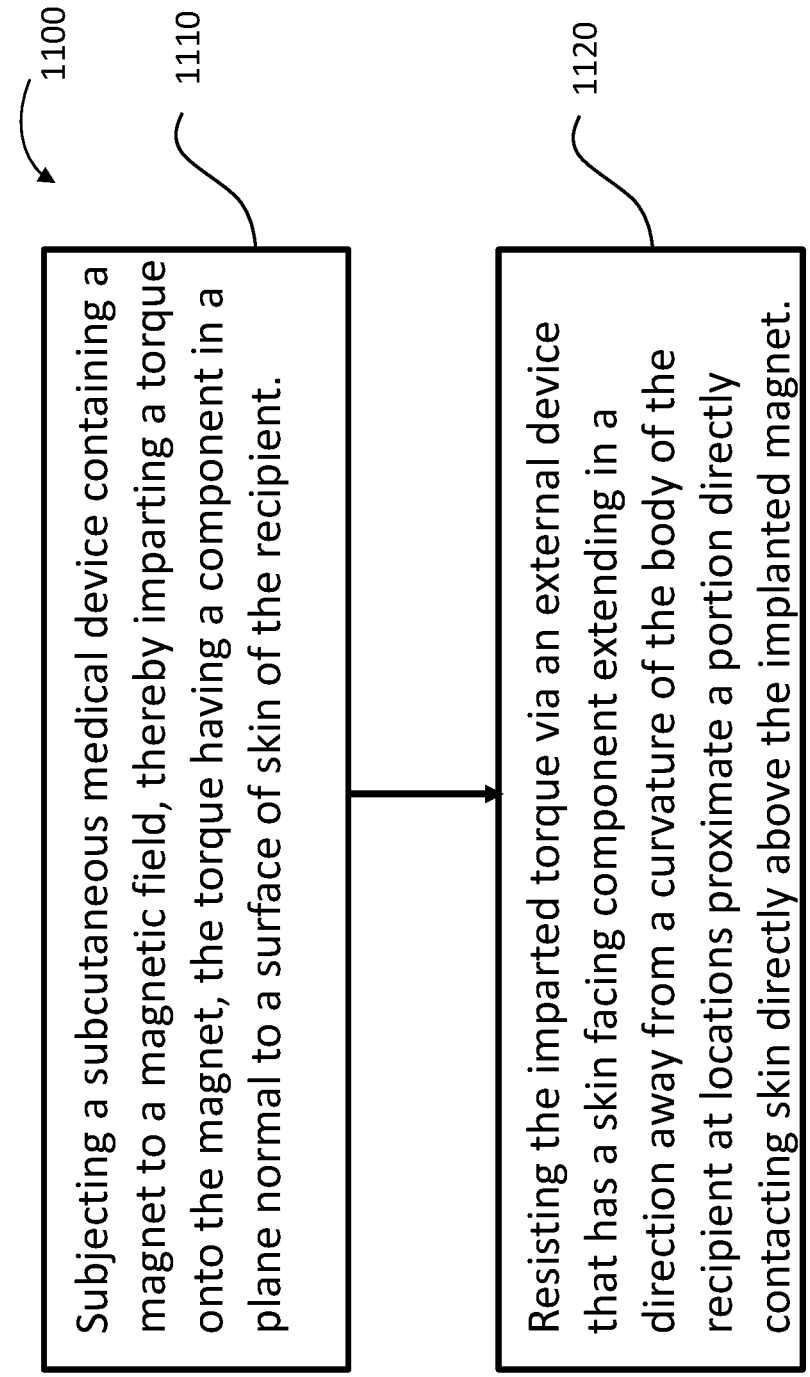
FIG. 11 presents an exemplary flowchart for an exemplary method according to an exemplary embodiment.

In view of the above, it is to be understood that some exemplary embodiments include methods of resisting the torque applied to a magnet implanted in a recipient when that magnet is subjected to an MRI magnetic field. In this regard, FIG. 11 depicts an exemplary algorithm 1100 for an exemplary method. Method 1100 includes method action 1110, which entails subjecting a subcutaneous medical device containing a magnet to a magnetic field. In this exemplary embodiment, the magnetic field imparts a torque on to the magnet, the torque having a component in a plane normal to a surface of the skin of the recipient (e.g., torque T1 of FIG. 4). This as opposed to a torque that is in the plane that is parallel to the tangent surface of the skin for example, which would cause the magnet to spin about axis 599 (as opposed to moving the angle of axis 599). Method 1100 further includes method action 1120, which entails the action of resisting the imparted torque via an external device (e.g., the assembly of belt 540 and splint 850) that has a skin facing component (e.g., the bottom surface of splint 850) extending in a direction away from a curvature of the body of the recipient at locations proximate a portion directly contacting skin directly above the implanted magnet. In this regard, this can correspond to those portions outside L81 of FIG. 8. That is, the portions that are directly contacting skin above the implanted magnet are encompassed by L81/the area 902 or 1002, and the portions that extend away from the skin of the portions outside of L81/the area 901 or 1001.

In an exemplary embodiment, the external device has a skin facing surface (e.g., the portion of the bottom of splint 850) that has an outer perimeter, wherein at least one location at the outer perimeter is anywhere from about 1 mm to about 15 mm away from a surface of the skin of the recipient. In an exemplary embodiment, the external device has a skin facing surface that has an outer perimeter, wherein at least a first location at the outer perimeter is anywhere from about 1 mm to about 15 mm away from a surface of the skin of the recipient and at least a second location at the outer perimeter is anywhere from about 1 mm to about 15 mm away from surface of the skin of the recipient, the first and second locations being opposite one another with respect to the perimeter. In an exemplary embodiment, the aforementioned first location corresponds to, with respect to FIG. 8, the left most portion of the splint 850, and the second location corresponds to the right most portion of the splint 850.

Figure 12:
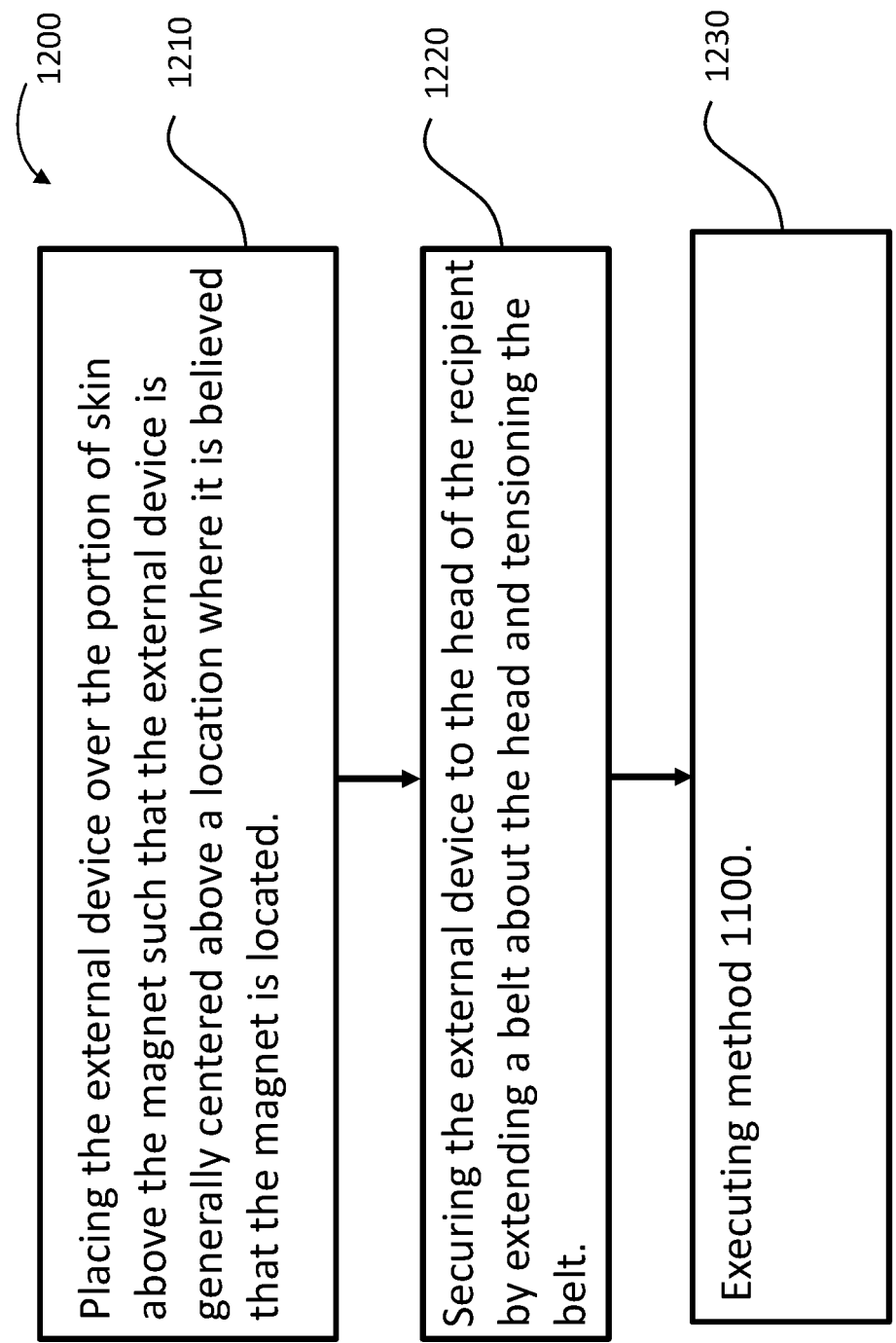
FIG. 12 presents an exemplary flowchart for an exemplary method according to an exemplary embodiment.

FIG. 12 presents another algorithm for an exemplary method, method 1200. As can be seen, method 1200 includes method action 1210, which entails placing the external device over the portion of skin above the magnet such that the external device is generally centered above a location where it is believed that the magnet is located. As noted above, in at least some exemplary embodiments, the healthcare professional placing the splint 850 against the head of the recipient may not necessarily know exactly where the magnet is located. Thus, the action of placing the external device over the portion of the skin by the magnet is done in a manner that is generally centered above a location where it is believed that the magnet is located. That is, method action 1210 does not require that the exact location be identified where that the splint 850 be exactly centered over the magnet.

Method 1200 further includes method action 1220, which entails securing the external device to the head of the recipient by extending a belt about the head and tensioning the belt. As noted above, the belt can be a general bandage or can be a specific apparatus specially designed for this method. By way of example only and not by way of limitation, the splint 850 can have holes located at the opposite ends in the length direction through which a nylon webbing extends, and the nylon webbing can have a belt buckle like device or a Velcro device to enable the tensioning, or more accurately, the maintenance of the tension on the belt. In this regard, FIG. 19 depicts an exemplary embodiment of an MRI splint that includes an adjustable Velcro belt 1940 and a splint 1950 which can correspond to any of the splints detailed herein and/or variations thereof. In the embodiment depicted in FIG. 19, the belt 1940 is attached to the very ends of the splint 1950. In an alternate embodiment, the belt 1940 extends about the top surface of the splint 1950 so as to encircle the splint 1950, albeit with the splint 1950 located on the inside diameter of the belt 1940. The belt 1940 can be used to hold the splint in position over the implant magnet while a supplementary bandage or similar restraint is used to apply sufficient compressive force for the MRI procedure. Alternately, the belt 1940 illustrated in FIG. 19 can be used in at least some embodiments to apply sufficient compressive force without supplementary bandaging. Some additional details of the utilization of Velcro or other types of belts can be utilized in at least some exemplary embodiments. Any device, system, and/or method that will enable the splint to be adhered to the skin of the recipient so as to enable the teachings detailed herein and/or variations thereof can be utilized in at least some exemplary embodiments.

The result of method action 1220 is that a cross-section taken on a plane normal to an axis of extension of the loop formed by the belt is such that there are two locations where the assembly formed by the belt and the external device are positioned away from skin of the recipient beyond that which results from hair being interposed between the assembly and the skin. These two portions are depicted in FIG. 8. It is noted that in an exemplary embodiment of method action 1220, these are the only two locations with respect to the aforementioned cross-section that are positioned away from skin of the recipient beyond that which results from hair being interposed between the assembly and the skin. In an exemplary embodiment, the aforementioned cross-section is taken on a plane normal to the axis of extension of the loop. That said, in an alternate embodiment, the aforementioned cross-section can be taken on a plane that is parallel to the axis of extension of the loop and lying thereon (such would capture the embodiment of FIG. 10, where all portions of the perimeter extent away from skin of the recipient/do not apply pressure to skin of the recipient). That said, in an alternate embodiment, the aforementioned cross-section can be taken on a plane that is parallel to the axis of extension of the loop, but does not lie thereon (such would capture the embodiment of FIG. 9, for example, because the plane would pass through the area 901).

Method 1200 further includes method action 1230, which entails executing method 1100.

Corollary to the above is that some methods according to the teachings detailed herein entail securing the external device to the head of the recipient by extending a belt about the head and tensioning the belt, wherein the force applied to skin of the recipient that resists the imparted torque is greater than that which would otherwise be the case without the skin facing components extending in the direction away from the curvature of the body. In this regard, this method action can be achieved by utilizing the phenomenon associated with decreasing the angle A1 as noted above. In an exemplary embodiment, the resulting force is at least 1.25 times greater than that which would be the case without the skin facing components extending as detailed. In an exemplary embodiment, the resulting force is at least 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, or 2.0 times, or more greater than that which would be the case without the skin facing components extending as detailed, or any value or range of values therebetween in 0.01 increments.

As noted above, the teachings detailed herein can enhance the resistance to the torque applied to the magnetic field beyond that which would result from the skin alone, the implanted medical device alone and/or the bandage of the embodiment of FIG. 5 alone. Still further, in at least some exemplary embodiments, as detailed above, the subcutaneous medical device is configured such that the magnet is removable from the subcutaneous medical device (e.g., through hole 180) by deforming silicone in an elastic manner, which silicone positions the magnet, without removing the subcutaneous medical device. In an exemplary embodiment, the medical device is configured such that the magnet can then be replaced. Such a feature can have utilitarian value with respect to a scenario where prior to subjecting the recipient to a magnetic field of an MRI machine, such as a magnetic field corresponding to, for example, 1 T or more (e.g., 1.5 T), the magnet is surgically removed. Then, after the recipient is subjected to an MRI magnetic field (and thus the remaining portions of the implant are also subjected to the MRI magnetic field), another surgery is executed to replace the magnet (which also includes placing a new magnet at the location of the old magnet) so that the full utilitarian value with respect to the implant can be achieved. Accordingly, the teachings detailed herein can be applicable to such a subcutaneous medical device, where instead of removing the magnet prior to subjecting the implantable component to the MRI magnetic field, the teachings detailed herein are applied so as to render such surgery unnecessary. In view of the above, in at least some exemplary embodiments, the action of subjecting the subcutaneous medical device containing the magnet to the magnetic field entails subjecting the magnet to at least a 1.5 T magnetic field without magnet dislocation. That is, the magnet may move a bit in some instances, but the magnet will not be dislocated from the housing of the implant containing the magnet. In an exemplary embodiment, the method is executed with respect to the aforementioned magnetic field, and the housing of the implant only elastically deforms. That is, in an exemplary embodiment, there is no plastic deformation of the housing. In an exemplary embodiment, any plastic deformation of the housing that occurs is de minimis from a standpoint of continued use of the implantable component. In an exemplary embodiment, the aforementioned scenarios result with respect to a magnetic field that corresponds to or more than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 T, or any values or range of values therebetween in 0.05 T increments.

Figure 13:
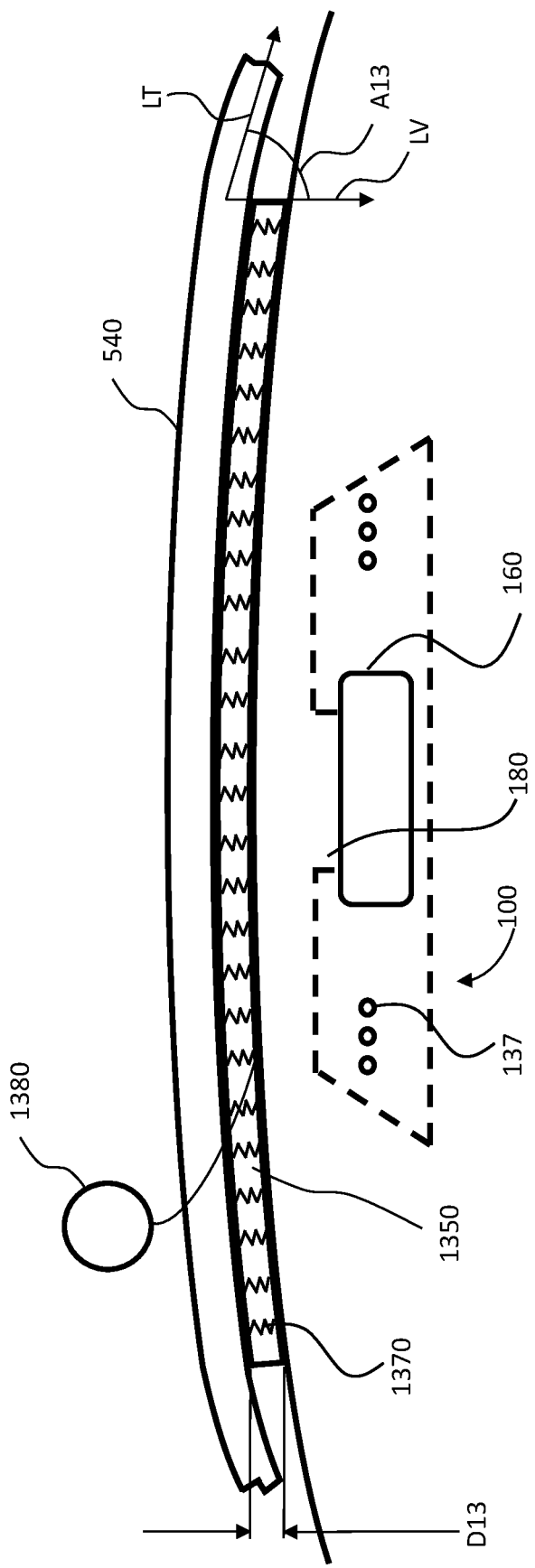
FIG. 13 depicts a cross-sectional view of another exemplary MRI splint assembly according to an exemplary embodiment.
Figure 14:
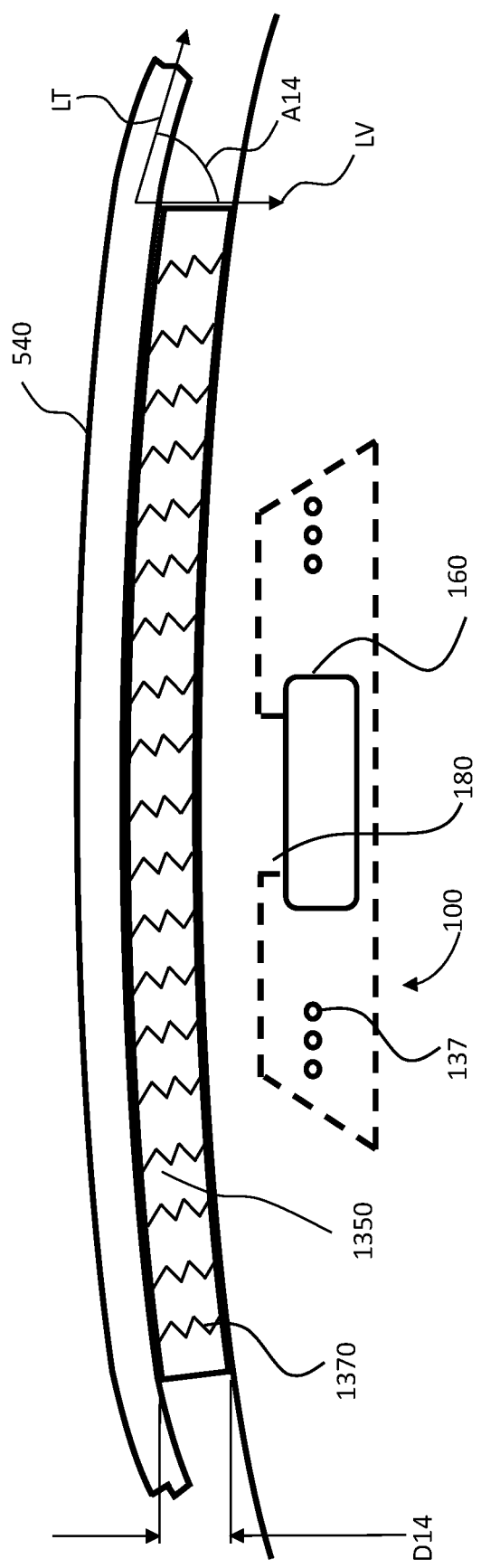
FIG. 14 depicts a cross-sectional view of the exemplary MRI splint of FIG. 13 after actuation of an energy storage device thereof.

FIG. 13 presents another exemplary embodiment of an enhanced splint, splint 1350. Here, splint 1350 is an energy storage device configured to store energy while the belt 540 is fastened around the recipient's head, and then, after the tension in the belt 1340 is stabilized (e.g., after the healthcare professional is done securing the belt 540 to the recipient such that the splint 1350 is fixed to the recipient, the energy stored in the splint 1350 is released, thus increasing the force applied to the skin of the recipient by the splint and the belt relative to that which would be the case in the absence of the release of the stored energy. In the exemplary embodiment of FIG. 13, the splint 1350 includes springs 1370 which are depicted in their compressed state, such that the distance from belt to the skin at the perimeter of the splint is D13, as can be seen. FIG. 13 depicts the splint 1350 prior to the release of the energy and after the belt 540 is secured to the recipient in its final position with respect to any adjustments made to the belt with respect to establishing the tensioned loop about the head of the recipient—when the energy storage device releases its energy, the belt will be moved in at least some exemplary embodiments. FIG. 14 depicts the splint 1350 after the release of the energy. Here, it can be seen that the springs 1370 have expanded, thus pushing the belt away from the skin of the recipient at the locations at the perimeter of the splint such that the distance is now D14. In an exemplary embodiment, the distance D13 is initially 2 mm, and the final distance D14 is 4 mm. in an exemplary embodiment, the ratio of D14 to D13 is about more than about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 3.1, 3.2, 3.3, 3.4, 3.5, 3.6, 3.7, 3.8, 3.9, or 4, or any value or range of values therebetween in 0.05 increments.

Corollary to this is that the angle A13 is decreased to a new angle, A14, which is less than A13. This thus increases the LV for the given tension LT. Note further that in an exemplary embodiment, the tension LT is also increased because the local portions of the belt 540 are pushed away from the skin as can be seen. Thus, embodiments can have a synergistic effect with respect to increasing LV not only because the angle A14 is less than A13, but because the component LT is increased with respect to that which was the case prior to the release of the energy. Thus, by increasing the LV, the downward force on to the skin over the magnet 160 is increased relative to that which is the case prior to the release of the energy.

In an exemplary embodiment, the force LV is at least 5%, 6%, 7%, 8%, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 160, 170, 180, 190, 200, 225, 250, 275, or 300%, or more, or any value or range of values therebetween in 0.1% increments greater (e.g., 5.5% greater, 33.33% greater, 8.2% to 22.2% greater, etc.) than that which was the case prior to the release of the energy of the splint 1350.

In an exemplary embodiment, the angle A14 is reduced from the angle A13 by at least about 1%, 2%, 3%, 4%, 5%, 6%, 7%, 8%, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or about 40%, or more, or any value or range of values therebetween in 0.1% increments due to the fact that the perimeter of the enhanced splint 850 is uplifted away from the skin upon the release of the energy of the splint 1350.

Still with reference to FIG. 13, as can be seen, there is a ring 1380 attached to a lanyard. In an exemplary embodiment, the splint 1350 is configured such after splint 1350 is positioned over the skin of the recipient and then fastened to the recipient via the belt 540, the healthcare professional pulls the ring 1380, and thus the lanyard, so as to release the springs from their compressed state to an expanded state. In an exemplary embodiment, the lanyard 1380 can be a heavy-duty thread that is pullable through the holes of a seam holding that the faces of the splint together/or otherwise close to each other such that the springs are compressed. Upon the removal of this heavy-duty thread, the seams are eviscerated, and thus the springs are capable of expanding, thus releasing the energy. In an alternate embodiment, a quasi-flexible pin can extend from one side of the splint to the other side of the splint, where interleaving flanges having respective holes therethrough are aligned such that the pen extends the holes, thus holding the faces of the splint together/or otherwise close to each other. Upon the removal of the pen, there is nothing that holds the flanges in place, and thus the faces spring apart from one another.

According to another exemplary embodiment, a heat sensitive adhesive or the like, or a light/UV sensitive adhesive or the like is present to hold the faces together/closer to each other. Upon the application of heat (or the application of an icepack) or upon the application of light or radiation of a certain frequency, the adhesive will degrade, thus allowing the springs to extend. Any device, system, and/or method that can enable the energy of the springs or the like to be stored, and then released at a desirable time can be utilized in at least some exemplary embodiments.

Figure 15:
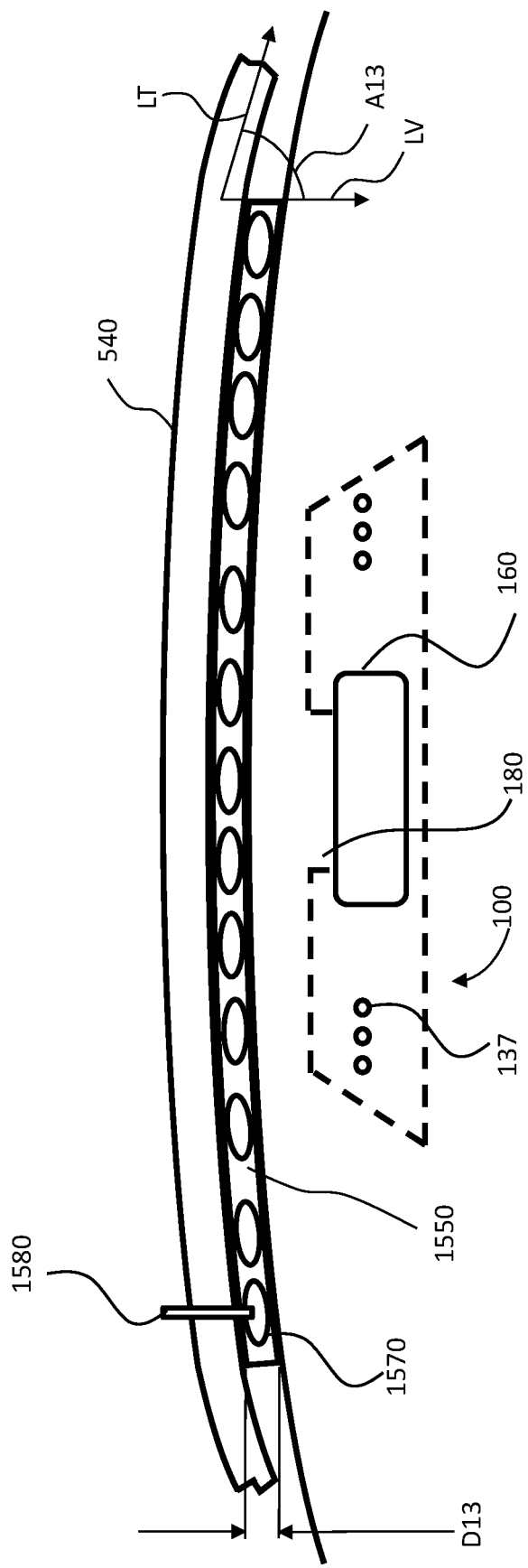
FIG. 15 depicts a cross-sectional view of another exemplary MRI splint assembly according to an exemplary embodiment.
Figure 16:
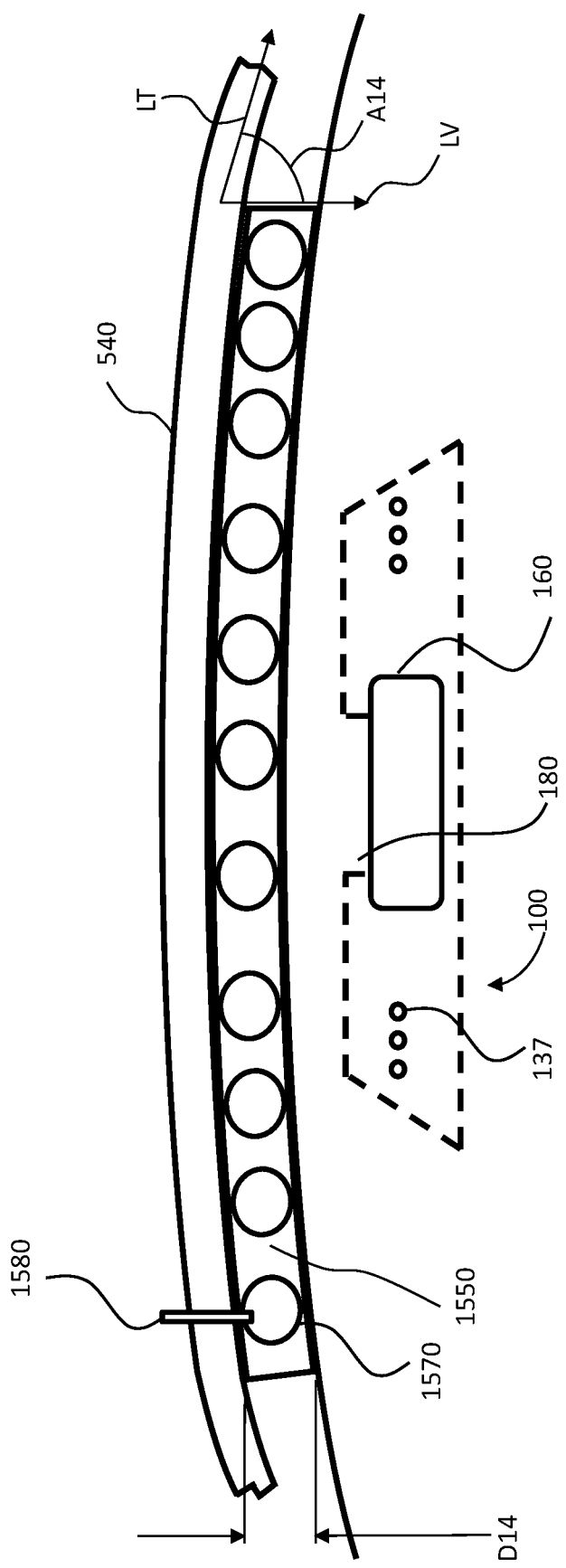
FIG. 16 depicts a cross-sectional view of the exemplary MRI splint of FIG. 15 after pressurization of the fluidic tubes thereof.

FIG. 15 depicts an alternate embodiment of a splint 1550. Here, a pneumatic or a fluidic flexible/expandable tubing system 1570 is located inside the splint 1550. In an exemplary embodiment, a fluid, such as air, or a liquid, is pumped under pressure via inlet 1580. As the fluid is pumped into the tubing system 1570, the tubing system expands, thus pushing the faces of the splint 1550 away from each other, as can be seen in FIG. 16. In an exemplary embodiment, the system can be calibrated such that for a certain pressure registered at the inlet 1580, the amount of force LV can be estimated. This way, the amount of force that is applied over the skin of the recipient can be controlled/adjusted to a desired amount by controlling the pressure at the inlet 1580. This as opposed to the more random results from applying a generalized tension on the belt 540. That said, in an alternate embodiment, a check valve can be utilized that pops upon the application of a given pressure inside the tubing system 1570. In this regard, a healthcare professional can apply compressed air or a pressurized fluid to the tubing system 1570. The system will be continuously pressurized until the check valve pops, after which no further pressure increase can be provided. This will have the effect of obtaining a generally repeatable pressure/force over the skin of the recipient from recipient to recipient, because the pressure at which the check valve pops will be the same every time. Note further that in an exemplary embodiment, instead of an external source of pressure/fluid, a compressed gas source can be provided with the splint 1550. Alternatively, and/or in addition this, a minor chemical reaction can be utilized to the fluid inside the tubing system 1570. Via the use of the aforementioned check valves, a safety feature can be provided.

Note further that the concept of controlling the force/pressure can be applied with respect to the spring embodiment. By way of example only and not by way of limitation, a mechanism that controls the distance that the faces of the splint can be moved relative to one another can be utilized, thus controlling the force/pressure that is applied to the skin of the recipient, at least providing that the control of the faces is such that the faces are prevented from extending the distance that will correspond to the full extent of the springs (i.e., when the springs are fully relaxed).

Any device, system, or method that can enable the force applied to the skin via the splint to be variable after the belt is tensioned can be utilized in at least some exemplary embodiments.

It is briefly noted that in an alternate embodiment, the MRI splint system can be provided with a device that provides an indication as to the force/pressure that is being applied to the skin of the recipient. In an exemplary embodiment, a gauge can be attached to the inlet 1580. Alternatively, and/or in addition to this, a pressure sensitive material that changes color with respect to pressure can be utilized to provide an indication of the pressure/force. This can be utilized with the embodiment of FIG. 13 or with the embodiment of FIG. 15. Alternatively, and/or in addition to this, a gauge that extends with increasing pressure can be utilized. For example, a gel can be pushed out of a cavity in the splint, where the volume of gel that is pushed out is related to the force/pressure that is applied to the skin of the recipient.

Thus, in an exemplary embodiment, there is an MRI splint that is configured for providing an indication to a user data indicative of a force applied to skin by the means for enhancing an interface with skin of the recipient.

Figure 17:
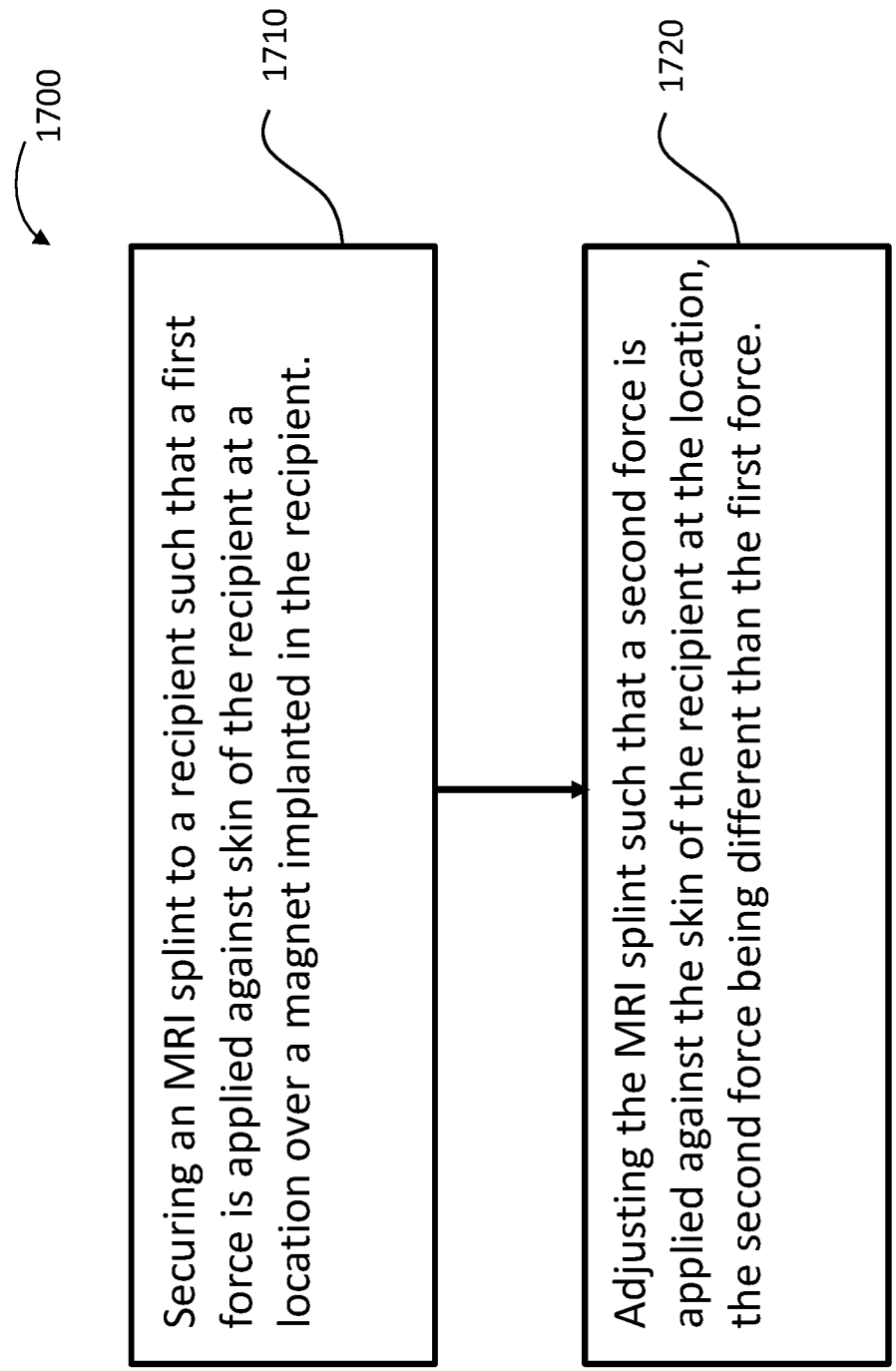
FIG. 17 presents an exemplary flowchart for an exemplary method according to an exemplary embodiment.

In view of the above, in an exemplary embodiment there is an exemplary method, as represented by, for example, the flowchart on FIG. 17. Method 1700 includes method action 1710, which entails securing an MRI splint to a recipient such that a first force is applied against skin of the recipient at a location over a magnet implanted in the recipient. In an exemplary embodiment, method action 1710 is executed by placing the splint over the magnet and tensioning the belt to a tension such that the splint is held or otherwise fastened to the recipient/no further direct adjustments to the belt will be applied. In an exemplary embodiment, this is executed by placing the splint of the magnet, and wrapping surgical gauze about the recipient's head such that the splint is trapped between the gauze and the skin of the recipient in a very snug manner. Method 1700 further includes method action 1720, which entails subsequent to the action of securing, adjusting the MRI splint such that a second force is applied against the skin of the recipient at the location, the second force being different than the first force. In an exemplary embodiment, method action 1720 is executed via the release of the energy of the splint 1350 as detailed above. Alternatively, and/or in addition to this, method action 1720 is executed via the introduction of a fluid under pressure into the fluid tubes of splint 1550. That said, in an alternative embodiment, method action 1720 can be executed so as to reduce the amount of pressure that was applied or otherwise results at the end of method action 1710. In this regard, in an exemplary embodiment, in a scenario where the belt was tightened by too much, the pressure relief valve detailed above with respect to the embodiment of FIG. 15 can be utilized to reduce or otherwise relieve the pressure. That said, in at least some exemplary embodiments, the aforementioned second force is greater than the first force, and in at least some exemplary embodiments, the second force is at least about two times greater than the first force.

In an exemplary embodiment, the MRI splint is configured to apply a constant force to skin of the recipient irrespective of a tension in the belt (which can correspond to a means for securing the splint 1550, which can correspond to a means for enhancing an interface with skin of the recipient.

In an exemplary embodiment, the action of adjusting the MRI splint (method action 1720) increases the tension in the belt relative to that which was the case at the time that the MRI splint was secured to the recipient. That is, LT is increased. This can be a result of the fact that the belt 540 is pushed further away from the skin of the recipient as a result of the actuation of the splint 1350 as detailed above.

As detailed above, exemplary embodiments are such that the resulting forces that are applied to the skin of the recipient are generally the same from recipient to recipient, even though a different MRI splint and a different belt is utilized for each recipient (although such does not have to be the case) and each recipient has a different sized head. Accordingly, in an exemplary embodiment, there is an exemplary method of executing method 1700 ten (10) times. In this exemplary embodiment, method action 1710 is executed ten (10) times such that the respective first forces are different from one another for each time that method action 1710 is executed. Method action 1720 is also executed ten (10) times such that the respective second forces are the same as one another for each time that method action 1720 is executed. In an exemplary embodiment, this can be achieved by utilizing the pertinent embodiments detailed herein and/or variations thereof. In an exemplary embodiment, instead of these method actions being executed 10 times, the method actions are executed 5 times, 6 times, 7 times, 8 times, 9 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 35 times, 40 times, 45 times, 50 times, or more where the various forces are the same and different as detailed above for the scenario where the method actions are executed 10 times.

In this regard, in an exemplary embodiment, it can be seen that the action of adjusting the MRI splint can compensate for resulting compression force against the skin of the recipient that results from the tensioning of the belt. This compensation can be an increase in the amount of force applied to the skin, or can be a decrease in the amount of force applied to the skin. That said, in an exemplary embodiment, if the tensioning is just right, there will be no increase or decrease in the force that is applied to the skin.

In an exemplary embodiment, method 1700 and the various sub methods detailed herein and variations thereof are executed, and then the recipient is subjected to a magnetic field of an MRI machine at magnetic field strengths detailed herein without magnet dislocation/without plastic deformation of the housing containing/retaining the magnet. In this regard, any of the features associated with the embodiments of FIG. 8 detailed above can be applicable to the embodiments of FIGS. 13-16. Indeed, it is noted that while the embodiments of FIGS. 13-16 have been presented in terms of a splint 1350 that is in contact with the skin of the recipient (or the hair over the recipient such that the hair is compressed so as to render the splint in effective contact with the skin of the recipient) over the entire skin facing side of the splint, concomitant with the embodiment of FIG. 6 detailed above, in an alternate embodiment, the splint has the liftoff portions concomitant with the embodiment of FIG. 8.

Consistent with the teachings detailed above with respect to utilizing the ripcord embodiments, etc., in an exemplary embodiment, the action of adjusting the MRI splint is such that the application of the second force against the skin is executed automatically after a manual initiation.

It is further noted that in an exemplary embodiment, there is an MRI splint configured such that a lashing angle of the belt (i.e., angle A13, A14, etc.) is increased automatically upon manual initiation of adjustment features of the means for enhancing an interface.

Figure 18:
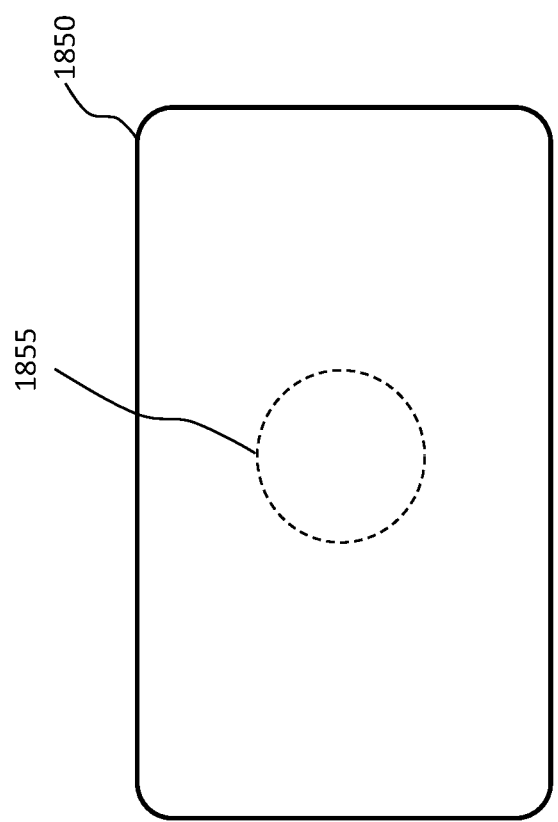
FIG. 18 presents an exemplary embodiment of an exemplary MRI splint.

FIG. 18 provides another exemplary embodiment having utilitarian value according to the teachings detailed herein. Here, in this exemplary embodiment, a magnet 1855 is embedded or otherwise located on the splint 1850, which can correspond to any of the splints detailed herein and/or variations thereof. This magnet is a low strength magnet but one that has poles that are properly aligned with the magnet implanted in the recipient such that the fact is that the magnet 1855 aligns the splint 1850 with the implanted magnet, thus centering the splints 1850 over the implanted magnet. In an exemplary embodiment, a healthcare professional applies the splint 1850 against the side of the head of the recipient. If the poles of the magnet are aligned with those of the magnet implanted in the recipient, the splint 1850 adheres to the head of the recipient. If not, the splint will repel, and thus the healthcare professional simply flips the splint over to the other side. Thus, in an exemplary embodiment, there is a device that automatically aligns with the magnet implanted in the recipient. In some alternate embodiments, instead of a magnet, a ferromagnetic material that is not a magnetic is utilized. This will provide at least partial alignment with the magnet implanted in the recipient. Via carefully adjusting the position of the splint 1850, the healthcare professional can obtain a reasonably good centering of the splint 1850 over the magnet. In this regard, the magnetic attraction will always be greatest when the center of the ferromagnetic material is directly over the center of the implanted magnet. Via a touch and feel method, the healthcare professional can obtain a rather accurate centering of the splint 1850. Thus, in an exemplary embodiment, the MRI splint includes a means for generally automatically aligning the splints over a magnet implanted in the recipient, where the "general" caveat affords for the scenario where the component 1855 is not a magnet is instead a ferromagnetic material.

In an exemplary embodiment, there is a method, comprising securing an MRI splint to a recipient such that a first force is applied against skin of the recipient at a location over a magnet implanted in the recipient, and subsequent to the action of securing, adjusting the MRI splint such that a second force is applied against the skin of the recipient at the location, the second force being different than the first force. In exemplary embodiment of this embodiment, the action of adjusting the MRI splint is such that the second force is applied against the skin automatically after a manual initiation. In an exemplary embodiment of this embodiment, the action of adjusting the MRI splint entails tensioning a belt securing the MRI splint to the recipient thus causing the MRI splint to flex towards the head of the recipient upon tensioning such that the MRI splint has a radius of curvature that is greater than a localized radius of curvature of skin of the recipient at the location where the MRI splint interfaces with skin of the recipient upon tensioning of the belt.

In an exemplary embodiment, an MRI splint assembly, comprising means for enhancing an interface with skin of the recipient at a location overlying an implanted magnet of an implantable component; and means for securing the means for enhancing an interface with skin of the recipient to the recipient, wherein the MRI splint assembly is configured to be secured to a head of the recipient. In an exemplary embodiment of this embodiment, the means for enhancing an interface is configured to adjust a force applied to the skin irrespective of adjustments resulting from the means for securing. In an exemplary embodiment of this embodiment, the means for enhancing an interface includes a spring loaded component that the means for enhancing an interface is a semi-flexible component. In an exemplary embodiment of this embodiment, the means for interfacing with skin of the recipient has a thickness to length aspect ratio of at least 0.01. In an exemplary embodiment of this embodiment, the means for enhancing an interface has a thickness to length aspect ratio of at least 0.012 and the means for enhancing an interface is substantially entirely made of ABS. In an exemplary embodiment of this embodiment, the MRI splint assembly is configured for providing an indication to a user data indicative of a force applied to skin by the means for enhancing an interface. In an exemplary embodiment of this embodiment, the means for enhancing an interface includes a spring loaded component that expands upon activation thereof.

It is further noted that in at least some exemplary embodiments, the splint surface is augmented so as to make handling thereof easier relative to that which be the case with a perfectly smooth surface. By way of example only and not by way of limitation, in an exemplary embodiment, ribs, bumps, and/or a roughened surface is provided to the top surface of the splint (i.e., the surface facing away from the skin of the recipient). In an exemplary embodiment, these are molded into the splint (e.g., the splint is still a one piece/monolithic component), while in other embodiments, these are features that are added to the underlying component that corresponds to the splint. In an exemplary embodiment, these features are adhered to the far surface of the splint by way of an adhesive or the like. That said, in an alternate embodiment, a co-molding process can be utilized so that there is a softer material on one side of the splint/a material that is more easily gripped on one side of the splint.

Still further, the aforementioned features enhancing the grip with respect to a user manipulating the splint can also have utilitarian value with respect to application to the skin facing side of the splint. Not only will this enhance the handling of the splint, but also it can in some embodiments, render the splint less likely to slide away from the location over the magnet after the splint is located over the magnet. Indeed, the nature of hair over the skin will enhance the sliding effect of the splint relative to the skin. Thus, the aforementioned surfaces can have utilitarian value with respect to reducing or otherwise mitigating that sliding effect.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system.

It is noted that in at least some exemplary embodiments, any feature disclosed herein can be utilized in combination with any other feature disclosed herein unless otherwise specified. Accordingly, exemplary embodiments include a medical device including one or more or all of the teachings detailed herein, in any combination.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method, comprising:
subjecting a subcutaneous medical device containing a magnet to a magnetic field, thereby imparting a torque onto the magnet; and
resisting the imparted torque via an external device that has a skin facing component extending in a direction away from a curvature of a body of a recipient of the magnet at locations proximate a portion directly contacting skin directly above the magnet.

2. The method of claim 1, wherein:
the external device has a skin facing surface that has an outer perimeter, wherein at least one location at the outer perimeter is at least 1 mm away from a surface of the skin of the recipient.

3. The method of claim 1, wherein:
the external device has a skin facing surface that has an outer perimeter, wherein at least a first location at the outer perimeter is at least 1 mm away from a surface of the skin of the recipient and at least a second location at the outer perimeter is at least 1 mm away from surface of the skin of the recipient, the first and second locations being opposite one another with respect to the perimeter.

4. The method of claim 1, further comprising:
placing the external device over the portion of skin above the magnet such that the external device is generally centered above a location where the magnet is believed to be located;
securing the external device to a head of the recipient by extending a belt about the head, thereby forming a loop by the belt, and tensioning the belt, wherein
a cross-section taken on a plane normal to an axis of extension of the loop formed by the belt is such that there are two locations where an assembly formed by the belt and the external device are positioned away from skin of the recipient beyond that which results from hair being interposed between the assembly and the skin.

5. The method of claim 1, further comprising:
securing the external device to a head of the recipient by extending a belt about the head and tensioning the belt, wherein, the skin facing component applies a force to the skin of the recipient that resists the imparted torque while the skin facing component extends in a direction away from the curvature of the body of the recipient.

6. The method of claim 1, wherein:
the subcutaneous medical device is configured such that the magnet is removable from the subcutaneous medical device by deforming silicone that positions the magnet without removing the subcutaneous medical device from the recipient; and
the action of subjecting the subcutaneous medical device containing the magnet to the magnetic field includes subjecting the magnet to at least a 1.5 T magnetic field without magnet dislocation.

7. The method of claim 1, further comprising:
fixing the external device to a head of the recipient via a tension system, wherein the external device includes a semi-flexible component,
the semi-flexible component resists complete conformation with the head of the recipient when a full amount of tension is applied to the tension system, which the full amount of tension is used during the action of subjecting the subcutaneous medical device containing the magnet to the magnetic field.

8. A method, comprising:
securing an MRI splint to a recipient such that a first force is applied against skin of the recipient at a location over a magnet implanted in the recipient; and
subsequent to the securing of the MRI splint, adjusting the MRI splint such that a second force is applied against the skin of the recipient at the location, the second force being different than the first force.

9. The method of claim 8, wherein:
the second force is greater than the first force.

10. The method of claim 8, wherein:
the second force is at least 2 times greater than the first force.

11. The method of claim 8, wherein:
the action of securing the MRI splint to the recipient includes securing the MRI split to a head of the recipient using a belt;
the action of adjusting the MRI splint is executed after the action of securing the MRI splint; and
the action of adjusting the MRI splint is accomplished by increasing tension in the belt.

12. The method of claim 8, further comprising:
repeating the actions of securing an MRI splint and adjusting the respective MRI splint at least 10 times, wherein:
the respective first forces are different from one another; and the respective second forces are at least one of approximate to or the same as one another.

13. The method of claim 8, wherein:
the action of securing the MRI splint to the recipient includes applying tension to an apparatus that extends about a portion of the recipient; and
the action of adjusting the MRI splint compensates for a resulting compression force on the skin of the recipient resulting from the tensioning.

14. The method of claim 8, wherein:
the magnet is part of a subcutaneous medical device that is configured such that the magnet is removable from the subcutaneous medical device, by deforming silicone that positions the magnet, without removing the subcutaneous medical device from the recipient;
the method further includes subjecting the subcutaneous medical device containing the magnet to a magnetic field of at least a 1.5 T magnetic field without magnet dislocation.

15. An MRI splint assembly, comprising:
means for enhancing an interface with skin of a recipient at a location overlying an implanted magnet of an implantable component; and means for securing the means for enhancing an interface with skin of the recipient to the recipient, wherein the MRI splint assembly is configured to be secured to a head of the recipient of the implanted magnet.

16. The MRI splint assembly of claim 15, wherein:

the MRI splint assembly is configured to apply a constant force to skin of the recipient irrespective of a tension in the means for securing.

17. The MRI splint assembly of claim 15, wherein:

the MRI splint assembly includes a means for generally automatically aligning the means for enhancing an interface over a magnet implanted in the recipient.

18. The MRI splint assembly of claim 15, wherein:

the means for enhancing an interface has a rigidity that has a value between and inclusive of 0.03 Nm to 1.9 Nm.

19. The MRI splint assembly of claim 15, wherein:

the MRI splint assembly is configured such that a lashing angle of the means for securing is increased automatically upon manual initiation of adjustment features of the means for enhancing an interface.

20. The MRI splint assembly of claim 15, wherein:

the means for enhancing an interface recipient is a rectangular component that has a length, width and a thickness, the length and width forming a rectangular feature, the thickness being at least an order of magnitude less than the length and the width, the thickness being at least one (1) mm.

* * * * *